(12) United States Patent
Ford et al.

(10) Patent No.: US 8,076,304 B2
(45) Date of Patent: Dec. 13, 2011

(54) METHODS AND COMPOSITIONS FOR THE DIAGNOSIS AND TREATMENT OF CYCLIN A-1 ASSOCIATED CONDITIONS

(75) Inventors: Heide L. Ford, Denver, CO (US); Ricardo D. Coletta, São Paulo (BR); Arthur R. Pardee, Cambridge, MA (US); Justin Lamb, Cambridge, MA (US)

(73) Assignee: The Regents of the University of Colorado, Denver, CO (US)

( * ) Notice: Subject to any disclaimer, the term of this patent is extended or adjusted under 35 U.S.C. 154(b) by 755 days.

(21) Appl. No.: 11/113,644

(22) Filed: Apr. 25, 2005

(65) Prior Publication Data

US 2006/0078903 A1    Apr. 13, 2006

Related U.S. Application Data

(60) Provisional application No. 60/565,296, filed on Apr. 26, 2004.

(51) Int. Cl.
 *C12N 15/00* (2006.01)
 *C12N 15/11* (2006.01)
(52) U.S. Cl. ......................................... 514/44
(58) Field of Classification Search ....................... None
 See application file for complete search history.

(56) References Cited

U.S. PATENT DOCUMENTS

| | | | |
|---|---|---|---|
| 6,506,559 B1 | 1/2003 | Fire et al. | |
| 7,153,700 B1 * | 12/2006 | Pardee et al. | 436/501 |
| 2006/0019256 A1 * | 1/2006 | Clarke et al. | 435/6 |

FOREIGN PATENT DOCUMENTS

WO       WO0198537 A2   12/2001

OTHER PUBLICATIONS

Qi et al (Cancer Research, 2003, 63:8323-8329).*
Yu et al (Nature Medicine, Feb. 2004; Epub Jan. 4, 2004; 10:175-181).*
Colette et al (PNAS, Apr. 2004, 101:6478-6483).*
Katoh et al (Nucleic Acids Research, Supplement No. 3, 2003, p. 249-250).*
Chopra et al (Targets, Sep. 2002, 1:102-108).*
Aoki et al (Clinical and Experimental Pharmacology and Physiology, 2003, 30:96-102).*
Li et al (Nature, 2003, 426:247-254).*
Relaix et al.,"From insect eye to vertebrate muscle: redeployment of a regulatory network."(1999) Genes Dev 13, 3171-8.
Ozaki et al., "Six1 controls patterning of the mouse otic vesicle."(2004) Development 131, 551-62.
Zheng et al., "The role of Six1 in mammalian auditory system development"(2003) Development 130, 3989-4000.
Zuber et al:, "Giant eyes in Xenopus laevis by overexpression of XOptx2" (1999) Cell 98, 341-52.
Goudreau et al., "Mutually regulated expression of Pax6 and Six3 and its implications for the Pax6 haploinsufficient lens phenotype" (2002) Proc Natl Acad Sci USA 99, 8719-24.
Laflamme et al., The homeotic protein Six3 is a coactivator of the nuclear receptor NOR-1 and a corepressor of the fusion protein EWS/NOR-1 in human extraskeletal myxoid chondrosarcomas, Cancer Res, 63 p. 449-454 (2001).
Winchester at al., "Expression of a homeobox gene (SIX5) in borderline ovarian tumours"(2000) J Clin Pathol 53, 212-7.
Li et al., "Gene expression in Wilms' tumor mimics the earliest committed stage in the metanephric mesenchymal-epithelial transition"(2002) Am J Pathol 160, 2181-90.
Khan et al., "cDNA microarrays detect activation of a myogenic transcription program by the PAX3-FKHR fusion oncogene" (1999) Proc Natl Acad Sci U S A 96, 13264-9.
Ford et al., "Abrogation of the G2 cell cycle checkpoint associated with overexpression of HSIX1: a possible mechanism of breast carcinogenesis"(1998) Proc Natl Acad Sci U S A.
Laclef et al., "Altered myogenesis in Six1-deficient mice"(2003) Development 130, 2239-52.
Liu et al., "Cyclin A1 is required for meiosis in the male mouse" (1998) Nat Genet 20, 377-80.
Geng et al., "Cyclin E ablation in the mouse" (2003) Cell 114, 431-43.
Luzzi et al., "Multistep nature of metastatic inefficiency: dormancy of solitary cells after successful extravasation and limited survival of early micrometastases"(1998) Am Jof Pathology, 153:865 (1998).
Tuschl "Small interfering RNAs: a revolutionary tool for the analysis of gene function and gene therapy" Molecular Intervent. 2002; 2(3):158-67.
Caplen et al, "Specific inhibition of gene expression by small double-stranded RNAs in invertebrate and vertebrate systems" Proc Natl Acad Sci U.S.A. 2001; 98: 9742-7.
Elbashir et al., "Duplexes of 21-nucleotide RNAs mediate RNA interference in cultured mammalian cells" Nature. 2001; 411:494-8.
Elbashir et al., "RNA interference is mediated by 21- and 22-nucleotide RNAs" Genes Dev. 2001;15: 188-200.
Elbashir et al., "Functional anatomy of siRNAs for mediating efficient RNAi in *Drosophila melanogaster* embryo lysate" EMBO J. 2001; 20: 6877-88.
Holen et al, "Positional effects of short interfering RNAs targeting the human coagulation trigger Tissue Factor" Nucleic Acids Res 2002; 30:1757-66.
Gurrieri et al., "Loss of the tumor suppressor PML in human cancers of multiple histologic origins" (2004) Journal of the National Cancer Institute 96, 269-79.
Guo et al., "A novel DNA damage checkpoint involving post-transcriptional regulation of cyclin A expression" (2000) J Biol Chem 275, 1715-22.
Yang et al., (1999) Blood 93, 2067-74.
Romanowski et al., "Interaction of *Xenopus* Cdc2 x cyclin A1 with the origin recognition complex" (2000) J Biol Chem 275, 4239-43.
Muller et al., "Cloning of the cyclin A1 genomic structure and characterization of the promoter region. GC boxes are essential for cell cycle-regulated transcription of the cyclin Al gene" (1999) J Biol Chem 274, 11220-8.
Spitz et al., "Expression of myogenin during embryogenesis is controlled by Six/*sine oculis* homeoproteins through a conserved MEF3 binding site" (1998) Proc Natl Acad Sci U S A 95, 14220-5.

(Continued)

*Primary Examiner* — Laura B Goddard
(74) *Attorney, Agent, or Firm* — Medlen + Carroll, LLP

(57) ABSTRACT

The present invention relates to compositions and methods for cancer therapeutics. In particular, the present invention provides compositions and methods for inhibiting cancer metastasis by inhibiting cyclin A1.

2 Claims, 10 Drawing Sheets

OTHER PUBLICATIONS

Sweeney et al., "A distinct cyclin A is expressed in germ cells in the mouse" (1996) Development 122, 53-64.

Yang et al., "Functions of cyclin A1 in the cell cycle and its interactions with transcription factor E2F-1 and the Rb family of proteins" (1999) Mol Cell Biol 19, 2400-7.

Ford et al., "Cell cycle-regulated phosphorylation of the human SIX1 homeodomain protein" (2000) The Journal of Biological Chemistry 275, 22245-22254.

Agami et al., "Distinct initiation and maintenance mechanisms cooperate to induce G1 cell cycle arrest in response to DNA damage" (2000) Cell 102, 55-66.

Sauk et al., "Hsp47 and the translation-translocation machinery cooperate in the production of alpha 1(1) chains of type I procollagen" (1994) J Biol Chem 269, 3941-6.

* cited by examiner

METHODS AND COMPOSITIONS FOR THE DIAGNOSIS AND TREATMENT OF CYCLIN A-1 ASSOCIATED CONDITIONS

The following application claims priority to U.S. provisional application No. 60/565,296, filed Apr. 26, 2004, which is incorporated by reference herein in its entirety.

The present invention was made, in part, with government support under Grant No. 1R01CA095277-01 awarded by the National Institutes of Health. The government may have certain rights in the invention.

FIELD OF THE INVENTION

The present invention relates to methods and compositions for diagnosing and treating diseases caused by over-expression of cyclin A1 and Six1 homeoprotein including, but not limited to, carcinoma.

BACKGROUND OF THE INVENTION

The term cancer collectively refers to more than 100 different diseases that affect nearly every part of the body. Throughout life, healthy cells in the body divide, grow, and replace themselves in a controlled fashion. Cancer starts when the genes directing this cellular division malfunction, and cells begin to multiply and grow out of control. A mass or clump of these abnormal cells is called a tumor. Not all tumors are cancerous. Benign tumors, such as moles, stop growing and do not spread to other parts of the body. But cancerous, or malignant, tumors continue to grow, crowding out healthy cells, interfering with body functions, and drawing nutrients away from body tissues. Malignant tumors can spread to other parts of the body through a process called metastasis. Cells from the original tumor break off, travel through the blood or lymphatic vessels or within the chest, abdomen or pelvis, depending on the tumor, and eventually form new tumors elsewhere in the body.

Only 5-10% of cancers are thought to be hereditary. The rest of the time, the genetic mutation that leads to the disease is brought on by other factors. The most common cancers are linked to smoking, sun exposure, and diet. These factors, combined with age, family history, and overall health, contribute to an individual's cancer risk.

Several diagnostic tests are used to rule out or confirm cancer. For many cancers, a biopsy is the primary diagnostic tool. However, many biopsies are invasive, unpleasant procedures with their own associated risks, such as pain, bleeding, infection, and tissue or organ damage. In addition, if a biopsy does not result in an accurate or large enough sample, a false negative or misdiagnosis can result, often requiring that the biopsy be repeated. What is needed in the art are improved methods to specifically detect, characterize, and monitor specific types of cancer. Al though patient survival after cancer diagnosis has improved, cancer continues to contribute significantly to morbidity and mortality. What is particularly needed are methods for treating and monitoring therapies targeting carcinoma.

SUMMARY OF THE INVENTION

The present invention relates to methods and compositions for diagnosing and treating diseases caused by over-expression of cyclin A1 and Six1 homeoprotein including, but not limited to, carcinoma.

Homeobox genes comprise a family of transcription factors that are essential during normal development and are often dysregulated in cancer. In the course of experiments made in development of the present invention, the inventors have discovered that tissue-restricted cyclin A1 is a transcriptional target of the Six1 homeoprotein. Both genes are expressed in the embryonic but not the terminally differentiated mammary gland, and Six1 knockout mice show a dramatic reduction of cyclin A1 in the embryonic mammary gland. In addition, both genes are re-expressed in breast cancers. Six1 overexpression increases cyclin A1 mRNA levels and activity, cell proliferation and tumor volume, whereas Six1 downregulation decreases cyclin A1 mRNA levels and proliferation. Overexpression of Six1 in wild type mouse embryonic fibroblasts, but not in knockout variants lacking the cyclin A1 gene, induces cell proliferation. Moreover, inhibition of cyclin A1 in Six1 overexpressing mammary carcinoma cells decreases proliferation. Hence, cyclin A1 is required for the proliferative effect of Six1, and Six1 overexpression re-instates an embryonic pathway of proliferation in breast cancer by upregulating cyclin A1.

Accordingly, in some embodiments, the present invention provides a method for screening compounds, comprising: a) providing: i) a biological sample from a subject suspected of having carcinoma; ii) reagents for detection of cyclin A1; and iii) one or more test compounds; b) contacting said biological sample with said one or more test compounds; and c) detecting said cyclin A1 in said sample using said reagents. In some embodiments the test compound is a small molecule. In further embodiments the test compound is a drug. In other embodiments the test compound is selected from the list including, but not limited to, a naturally occurring peptide, a synthetic peptide, a non-peptide mimetic, an antibody, a nucleic acid, a small RNA duplex, a small interfering RNA (siRNA) molecule, or an antisense oligonucleotide. In some embodiments, the method further comprises the step of determining the efficacy of the drug based on said detecting. The present invention is not limited to the detection of a particular cyclin A1 ligand. Any suitable cyclin A1 ligand is contemplated including, but not limited to, a full-length ligand, a fragment of a full-length ligand, a modified ligand, or a conjugated ligand. The present invention is not limited to a particular assay. In some embodiments, said reagents comprise reagents for performing an immunoassay. Any suitable assay is contemplated including, but not limited to, ELISA, radioimmunoassay, automated immunoassay, cytometric bead assay, flow cytometry assay, and immunoprecipitation assay. In some embodiments, the ELISA assay is a quantitative ELISA assay.

In further embodiments, the test compound decreases the amount of said cyclin A1 in said biological sample. In other embodiments, test compound increases the amount of said cyclin A1 in said biological sample. In further embodiment, the test compound decreases the activity of said cyclin A1 in said biological sample. In still further embodiments, the test compound increases the activity of said cyclin A1 in said biological sample. In preferred embodiment, the test compound inhibits the interaction of a Six1 homeoprotein with cyclin A1. In other embodiments, the biological sample is an in vitro biological sample. In further embodiments the biological sample is an in vivo biological sample.

In yet other embodiments, the present invention provides a method of modulating cyclin A1 signaling, comprising: a) providing: i) a subject with one or more signs or symptoms of carcinoma; and ii) a preparation comprising a cyclin A1 antagonist; and b) administering said preparation to said subject under conditions such that cyclin A1 is modulated in said subject. In some embodiments said cyclin A1 modulation is modulation in the amount of cyclin A1. In other embodiments, said cyclin A1 modulation is modulation in the activity of cyclin A1. In some embodiments the cyclin A1 antagonist is a small molecule. In further embodiments the cyclin A1 antagonist is a drug. In other embodiments the cyclin A1 antagonist is selected from the list including, but not limited to, a naturally occurring peptide, a synthetic peptide, a non-peptide mimetic, an antibody, a nucleic acid, a small RNA duplex, a small interfering RNA (siRNA) molecule, or an antisense oligonucleotide. In preferred embodiments said cyclin A1 antagonist inhibits the interaction of a Six1 homeoprotein with cyclin A1. In particularly preferred embodiments, said subject has breast cancer.

The present invention further provides a composition comprising a compound that is a cyclin A1 antagonist that inhibits cyclin A1 alone or in combination with a chemotherapeutic agent. In some embodiments the compound is a small molecule. In further embodiments the compound is a drug. In other embodiments the compound is selected from the list including, but not limited to, a naturally occurring peptide, a synthetic peptide, a non-peptide mimetic, an antibody, a nucleic acid, a small RNA duplex, a small interfering RNA (siRNA) molecule that targets cyclin A1 expression, or an antisense oligonucleotide. In preferred embodiments said composition treats carcinoma in a subject.

In one embodiment, the present invention provides a method of treating cyclin A1-associated conditions comprising: a) providing: i) a subject with one or more symptoms of carcinoma, and ii) a preparation comprising a cyclin A1 antagonist; and b) administering said preparation to said subject. In one embodiment, said administration to said subject is under conditions such that said one or more signs and symptoms are improved.

In one embodiment said subject is an animal. In a further embodiment said animal is a mammal. In a still further embodiment, said mammal is a human.

In one embodiment, said cyclin A1 antagonist is a peptide. In a further embodiment, said peptide is a naturally occurring peptide. In a still further embodiment, said peptide is a synthetic peptide. In another embodiment, said cyclin A1 antagonist is a non-peptide mimetic (such as analogues, derivatives or mimetics of cyclin A1 antagonist peptides). In a still further embodiment said cyclin A1 antagonist is an antibody. In another embodiment, said antibody is an anti-cyclin A1 antibody. In other embodiments, said cyclin A1 antagonists are biologically active non-peptide compounds. In yet another embodiment, said cyclin A1 antagonist is a nucleic acid. In a particularly preferred embodiment, said nucleic acid is a small interfering RNA duplex, or vectors encoding said small interfering RNA duplex, configured to inhibit expression of cyclin A1. In another embodiment, said cyclin A1 antagonist is an antisense oligonucleotide. In a still further embodiment, said administering of said cyclin A1 antagonist is via gene therapy.

In one embodiment, the present invention provides a method of treating Six1-associated conditions comprising: a) providing: i) a subject with one or more symptoms of carcinoma, and ii) a preparation comprising a Six1 antagonist; and b) administering said preparation to said subject. In one embodiment, said administration to said subject is under conditions such that said one or more signs and symptoms are improved.

In one embodiment, said Six1 antagonist is a peptide. In a further embodiment, said peptide is a naturally occurring peptide. In a still further embodiment, said peptide is a synthetic peptide. In another embodiment, said Six1 antagonist is a non-peptide mimetic (such as analogues, derivatives or mimetics of Six1 antagonist peptides). In a still further embodiment said Six1 antagonist is an antibody. In another embodiment, said antibody is an anti-Six1 antibody. In other embodiments, said Six1 antagonists are biologically active non-peptide compounds. In yet another embodiment, said Six1 antagonist is a nucleic acid. In a particularly preferred embodiment, said nucleic acid is a small interfering RNA duplex, or vectors encoding said small interfering RNA duplex, configured to inhibit expression of Six1. In another embodiment, said Six1 antagonist is an antisense oligonucleotide. In a still further embodiment, said administering of said Six1 antagonist is via gene therapy.

A variety of modes of administration of the compounds of the present invention are contemplated. In some embodiments, said administration is parenteral (e.g. intravenous), in other embodiments, said administration is oral. In other embodiments, said administration is intranasal or respiratory. In yet other embodiments, said administration is cutaneous, transdermal or transmucosal (e.g. by application of a composition comprising the compounds of the invention to a body surface). In yet other embodiments, said administration is by injection directly to an affected area (e.g. a particular organ). A variety of pharmaceutically acceptable formulations are contemplated in the present invention. Among dosage forms contemplated (as appropriate for the mode of administration and desired target organ or tissue) are pills, tablets, lozenges, suspensions, aqueous or organic solutions, capsules, aerosols, creams, lotions, jellies, patches, powders and the like. Such dosage forms are formulated with pharmaceutically acceptable vehicles as is known in the art.

The dosage of the compositions used in the methods of the present invention (cyclin A1 antagonists, Six1 antagonists) is any that is effective to improve said one or more signs or symptoms of said subject. In some embodiments, the dosage is sufficient to attain a serum or local concentration in the range of approximately 0.5 µg/ml to approximately 500 µg/ml. In a preferred embodiment, the serum concentration is in the range of approximately 5 µg/ml to approximately 100 µg/ml, and even more preferably in the range of approximately 10 µg/ml to approximately 50 µg/ml.

In some embodiments, the present invention provides methods of detecting cyclin-A1 associated conditions, comprising: a) providing: i) a biological sample from a subject, wherein said subject is suspected of having carcinoma; ii) reagents for detection of a cyclin A1 ligand; and b) detecting the presence of said cyclin A1 ligand in said biological sample using said reagents. The present invention is not limited to a particular biological sample type. In one embodiment, the biological sample is a fluid selected from the list of blood, plasma, serum, urine, lymph, cerebrospinal fluid, bile, glandular secretion, or other fluid in a biological compartment. Any bodily fluid may be utilized. In a further embodiment, said biological fluid is a tissue aspirate. In a still further embodiment, said biological sample is a tissue biopsy, or tissue biopsy lysate. In some embodiments, detecting the presence of said cyclin A1 ligand in said biological sample comprises detecting the amount of said cyclin A1 ligand in said biological sample. In one embodiment, the said cyclin A1 ligand is a full-length ligand. In other embodiments, said cyclin A1 ligand is a fragment of the full-length ligand. The present invention is not limited to a particular assay. In some embodiments, said reagents comprise reagents for performing an immunoassay. Any suitable assay is contemplated including, but not limited to, ELISA, radio-immunoassay, automated immunoassay, cytometric bead assay, flow cytometery assay and immunoprecipitation assay. In some embodiments, the ELISA assay is a quantitative ELISA assay. In other embodiments, the present invention further comprises the step of determining a treatment course of action based on carcinoma risk. In some embodiments, the treatment course of action comprises administration of therapeutic agents. In other embodiments, the treatment course of action comprises serial monitoring of cyclin A1 ligand expression. In further embodiments, the treatment course of action comprises a surgical procedure.

In other embodiments, the present invention provides a kit, comprising: a) reagents for the detection of the amount of a cyclin A1 ligand in a biological sample from a subject; and b) instructions for using said reagents for detecting the presence of said cylcin A1 ligand in said biological sample. The present invention is not limited to the detection of a particular cyclin A1 ligand. Any suitable cyclin A1 ligand is contemplated including, but not limited to, a full-length ligand, a fragment of a full-length ligand, a modified ligand, or a conjugated ligand. The present invention is not limited to a particular assay. In some embodiments, said reagents comprise reagents for performing an immunoassay. Any suitable assay is contemplated including, but not limited to, ELISA, radio-immunoassay, automated immunoassay, cytometric bead assay, flow cytometry assay, and immunoprecipitation assay. In some embodiments, the ELISA assay is a quantitative ELISA assay. In some embodiments, the instructions comprise instructions required by the United States Food and Drug Administration for use in in vitro diagnostic products. In some embodiments, the instructions further comprise instructions for using said kit for diagnosing cyclin A1-associated conditions including, but not limited to, carcinoma. In other embodiments, the instructions further comprise instructions for using said kit for predicting the risk of cyclin A1-associated conditions including, but not limited to, carcinoma.

DESCRIPTION OF THE FIGURES

FIG. 10A shows that cyclin A1 mRNA measured by qRT-PCR is reduced in Six1 overexpressing 21PT cells after introduction of a cyclin A1 siRNA.

DEFINITIONS

Figure 1:
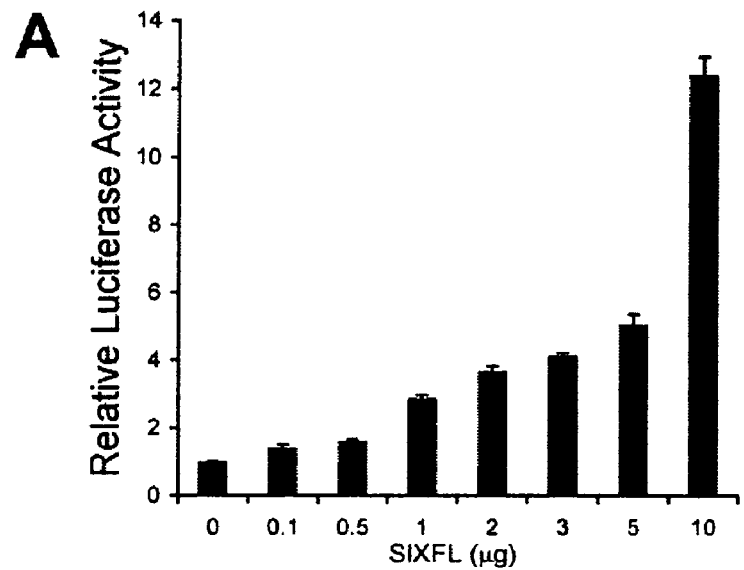
FIG. 1A shows levels of luciferase activity in MCF7 cells transfected with increasing concentrations of human Six1 expression plasmid plus the full length human cyclin A1 promoter-luciferase construct.
FIG. 1B shows that activation of the cyclin A1 promoter occurs through the region from −112 to −37 bp.
FIG. 1C shows CHIP assays performed with anti-Six1 antibody and control with analysis of the immunoprecipitates by cyclin A1 promoter-specific primers in the Six1 binding region (−207 to −18) or with primers upstream of the binding region (−2312 to −2107).
Figure 1:
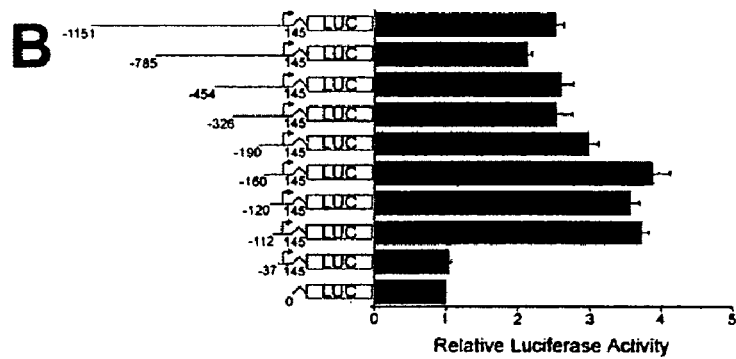
Figure 1:
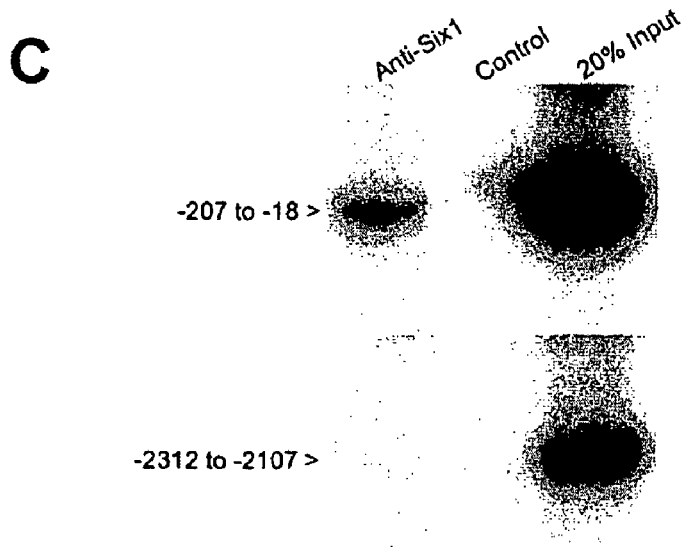

To facilitate an understanding of the present invention, a number of terms and phrases are defined below:

As used herein, the term "immunoglobulin" or "antibody" refer to proteins that bind a specific antigen. Immunoglobulins include, but are not limited to, polyclonal, monoclonal, chimeric, and humanized antibodies, Fab fragments, F(ab')$_2$ fragments, and includes immunoglobulins of the following classes: IgG, IgA, IgM, IgD, IgE, and secreted immunoglobulins (sIg). Immunoglobulins generally comprise two identical heavy chains and two light chains. However, the terms "antibody" and "immunoglobulin" also encompass single chain antibodies and two chain antibodies.

As used herein, the term "antigen binding protein" refers to proteins that bind to a specific antigen. "Antigen binding proteins" include, but are not limited to, immunoglobulins, including polyclonal, monoclonal, chimeric, and humanized antibodies; Fab fragments, F(ab')$_2$ fragments, and Fab expression libraries; and single chain antibodies.

The term "epitope" as used herein refers to that portion of an antigen that makes contact with a particular immunoglobulin.

When a protein or fragment of a protein is used to immunize a host animal, numerous regions of the protein may induce the production of antibodies which bind specifically to a given region or three-dimensional structure on the protein; these regions or structures are referred to as "antigenic determinants". An antigenic determinant may compete with the intact antigen (i.e., the "immunogen" used to elicit the immune response) for binding to an antibody.

The terms "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labeled "A" and the antibody will reduce the amount of labeled A bound to the antibody.

As used herein, the terms "non-specific binding" and "background binding" when used in reference to the interaction of an antibody and a protein or peptide refer to an interaction that is not dependent on the presence of a particular structure (i.e., the antibody is binding to proteins in general rather that a particular structure such as an epitope).

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "subject diagnosed with a cancer" refers to a subject who has been tested and found to have cancerous cells. The cancer may be diagnosed using any suitable method, including but not limited to, biopsy, x-ray, blood test, and the diagnostic methods of the present invention. A "preliminary diagnosis" is one based only on visual (e.g., CT scan or the presence of a lump) and antigen tests (e.g., PSA).

As used herein, the term "subject at risk for cancer" refers to a subject with one or more risk factors for developing a specific cancer. Risk factors include, but are not limited to, gender, age, genetic predisposition, environmental expose, and previous incidents of cancer, preexisting non-cancer diseases, and lifestyle. As used herein, the term "subject suspected of having carcinoma" refers to a subject with one or more signs or symptoms of carcinoma.

As used herein, the term "non-human transgenic animal lacking a functional Six1 or cyclin A1 gene" refers to a non-human animal (preferable a mammal, more preferably a mouse) whose endogenous Six1 or cyclin A1 gene has been inactivated (e.g., as the result of a "Six1 or cyclin A1 knock-out" or a "Six1 or cyclin A1 knock-in").

As used herein, the terms "Six1 or cyclin A1 knockout" refers to a non-human animal (e.g., a mouse) lacking a functional Six1 or cyclin A1 gene. In some embodiments, the entire Six1 or cyclin A1 gene is deleted. In other embodiments, the gene is inactivated via other means (e.g., deletion of essential portions or inversions of some or all of the Six1 or cyclin A1 gene). In other embodiments, the Six1 or cyclin A1 gene is inactivated using antisense inhibition. Six1 or cyclin A1 knockout include conditional knockouts (e.g., selective inhibition of gene activity). Six1 or cyclin A1 knockout mice may be made using any suitable method including, but not limited to, those described herein. Six1 or cyclin A1 genes can also be inactivated via the construction of a "Six1 or cyclin A1 knock-in" in which the gene is inactivated by the insertion of exogenous DNA into a region of the gene required for function.

As used herein, the term "mimetic" refers to a small molecule compound that mimics the binding of a Six1 or cyclin A1 to a ligand.

As used herein, the term "non-human animals" refers to all non-human animals including, but are not limited to, vertebrates such as rodents, non-human primates, ovines, bovines, ruminants, lagomorphs, porcines, caprines, equines, canines, felines, aves, etc.

As used herein, the term "gene transfer system" refers to any means of delivering a composition comprising a nucleic acid sequence to a cell or tissue. For example, gene transfer systems include, but are not limited to, vectors (e.g., retroviral, adenoviral, adeno-associated viral, and other nucleic acid-based delivery systems), microinjection of naked nucleic acid, polymer-based delivery systems (e.g., liposome-based and metallic particle-based systems), biolistic injection, and the like. As used herein, the term "viral gene transfer system" refers to gene transfer systems comprising viral elements (e.g., intact viruses, modified viruses and viral components such as nucleic acids or proteins) to facilitate delivery of the sample to a desired cell or tissue. As used herein, the term "adenovirus gene transfer system" refers to gene transfer systems comprising intact or altered viruses belonging to the family Adenoviridae.

As used herein, the term "site-specific recombination target sequences" refers to nucleic acid sequences that provide recognition sequences for recombination factors and the location where recombination takes place.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N-6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N-6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the term "transgene" refers to a heterologous gene that is integrated into the genome of an organism (e.g., a non-human animal) and that is transmitted to progeny of the organism during sexual reproduction.

As used herein, the term "transgenic organism" refers to an organism (e.g., a non-human animal) that has a transgene integrated into its genome and that transmits the transgene to its progeny during sexual reproduction.

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally occurring mutants can be isolated; these are identified by the fact that they have altered characteristics (including altered nucleic acid sequences) when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the terms "an oligonucleotide having a nucleotide sequence encoding a gene" and "polynucleotide having a nucleotide sequence encoding a gene," means a nucleic acid sequence comprising the coding region of a gene or in other words the nucleic acid sequence that encodes a gene product. The coding region may be present in a cDNA, genomic DNA or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "oligonucleotide," refers to a short length of single-stranded polynucleotide chain. Oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the terms "complementary" or "complementarity" are used in reference to polynucleotides (i.e., a sequence of nucleotides) related by the base-pairing rules. For example, for the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is a nucleic acid molecule that at least partially inhibits a completely complementary nucleic acid molecule from hybridizing to a target nucleic acid is "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous nucleic acid molecule to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that is substantially non-complementary (e.g., less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (See e.g., Anderson and Young, Quantitative Filter Hybridization, in Nucleic Acid Hybridization [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Under "low stringency conditions" a nucleic acid sequence of interest will hybridize to its exact complement, sequences with single base mismatches, closely related sequences (e.g., sequences with 90% or greater homology), and sequences having only partial homology (e.g., sequences with 50-90% homology). Under 'medium stringency conditions," a nucleic acid sequence of interest will hybridize only to its exact complement, sequences with single base mismatches, and closely relation sequences (e.g., 90% or greater homology). Under "high stringency conditions," a nucleic acid sequence of interest will hybridize only to its exact complement, and (depending on conditions such a temperature) sequences with single base mismatches. In other words, under conditions of high stringency the temperature can be raised so as to exclude hybridization to sequences with single base mismatches.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1×SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0×SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l $NaH_2PO_4 \cdot H_2O$ and 1.85 g/l EDTA, pH adjusted to 7.4 with NaOH), 0.1% SDS, 5×Denhardt's reagent [50×Denhardt's contains per 500 ml: 5 g Ficoll (Type 400, Pharamcia), 5 g BSA (Fraction V; Sigma)] and 100 µg/ml denatured salmon sperm DNA followed by washing in a solution comprising 5×SSPE, 0.1% SDS at 42° C. when a probe of about 500 nucleotides in length is employed.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.) (see definition above for "stringency").

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

"Amino acid sequence" and terms such as "polypeptide" or "protein" are not meant to limit the amino acid sequence to the complete, native amino acid sequence associated with the recited protein molecule.

The term "native protein" as used herein to indicate that a protein does not contain amino acid residues encoded by vector sequences; that is, the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

As used herein, the term "vector" is used in reference to nucleic acid molecules that transfer DNA segment(s) from one cell to another. The term "vehicle" is sometimes used interchangeably with "vector." Vectors are often derived from plasmids, bacteriophages, or plant or animal viruses.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "overexpression" and "overexpressing" and grammatical equivalents, are used in reference to levels of mRNA to indicate a level of expression approximately 3-fold higher (or greater) than that observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the mRNA-specific signal observed on Northern blots). The amount of mRNA present in the band corresponding in size to the correctly spliced transgene RNA is quantified; other minor species of RNA which hybridize to the transgene probe are not considered in the quantification of the expression of the transgenic mRNA.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, *Virol.*, 52:456 [1973]), has been modified by several groups to optimize conditions for particular types of cells. The art is well aware of these numerous modifications.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

As used herein, the term "selectable marker" refers to the use of a gene that encodes an enzymatic activity that confers the ability to grow in medium lacking what would otherwise be an essential nutrient (e.g. the HIS3 gene in yeast cells); in addition, a selectable marker may confer resistance to an antibiotic or drug upon the cell in which the selectable marker is expressed. Selectable markers may be "dominant"; a dominant selectable marker encodes an enzymatic activity that can be detected in any eukaryotic cell line. Examples of dominant selectable markers include the bacterial aminoglycoside 3' phosphotransferase gene (also referred to as the neo gene) that confers resistance to the drug G418 in mammalian cells, the bacterial hygromycin G phosphotransferase (hyg) gene that confers resistance to the antibiotic hygromycin and the bacterial xanthine-guanine phosphoribosyl transferase gene (also referred to as the gpt gene) that confers the ability to grow in the presence of mycophenolic acid. Other selectable markers are not dominant in that their use must be in conjunction with a cell line that lacks the relevant enzyme activity. Examples of non-dominant selectable markers include the thymidine kinase (tk) gene that is used in conjunction with tk⁻ cell lines, the CAD gene that is used in conjunction with CAD-deficient cells and the mammalian hypoxanthine-guanine phosphoribosyl transferase (hprt) gene that is used in conjunction with hprt⁻ cell lines. A review of the use of selectable markers in mammalian cell lines is provided in Sambrook, J. et al., Molecular Cloning: A Laboratory Manual, 2nd ed., Cold Spring Harbor Laboratory Press, New York (1989) pp. 16.9-16.15.

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

As used, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The terms "test compound" and "candidate compound" refer to any chemical entity, pharmaceutical, drug, and the like that is a candidate for use to treat or prevent a disease, illness, sickness, or disorder of bodily function (e.g., cancer). Test compounds comprise both known and potential therapeutic compounds. A test compound can be determined to be therapeutic by screening using the screening methods of the present invention.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water and industrial samples. Such examples are not however to be construed as limiting the sample types applicable to the present invention.

As used herein, the term "siRNAs" refers to small interfering RNAs. In some embodiments, siRNAs comprise a duplex, or double-stranded region, of about 18-25 nucleotides long; often siRNAs contain from about two to four unpaired nucleotides at the 3' end of each strand. At least one strand of the duplex or double-stranded region of a siRNA is substantially homologous to, or substantially complementary to, a target RNA molecule. The strand complementary to a target RNA molecule is the "antisense strand;" the strand homologous to the target RNA molecule is the "sense strand," and is also complementary to the siRNA antisense strand. siRNAs may also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants.

The term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial.

As used herein, the terms "anticancer agent," "conventional anticancer agent," or "cancer therapeutic drug" refer to any therapeutic agents (e.g., chemotherapeutic compounds and/or molecular therapeutic compounds), radiation therapies, or surgical interventions, used in the treatment of cancer (e.g., in mammals).

As used herein, the terms "drug" and "chemotherapeutic agent" refer to pharmacologically active molecules that are used to diagnose, treat, or prevent diseases or pathological conditions in a physiological system (e.g., a subject, or in vivo, in vitro, or ex vivo cells, tissues, and organs). Drugs act by altering the physiology of a living organism, tissue, cell, or in vitro system to which the drug has been administered. It is intended that the terms "drug" and "chemotherapeutic agent" encompass anti-hyperproliferative and antineoplastic compounds as well as other biologically therapeutic compounds.

As used herein, the term "Ad" refers to adenovirus. As used herein, the term "GFP" refers to green fluorescent protein. As used herein, the "MOI" refers to multiplicity of infection. As used herein, the term "MEF" refers to mouse embryonic fibroblast. As used herein, the term "RT-PCR" refers to reverse transcription-polymerase chain reaction. As used herein, the term "qRT-PCR" refers to quantitative real-time RT-PCR. As used herein, the term "BrdU" refers to bromodeoxyuridine. As used herein the term "CHIP" refers to chromatin immunoprecipitation.

DETAILED DESCRIPTION OF THE INVENTION

The present invention relates to methods and compositions for diagnosing and treating diseases caused by over-expression of cyclin A1 and Six1 homeoprotein including, but not limited to, carcinoma.

The molecular pathways involved in oncogenesis often represent aberrations of processes that normally occur during embryogenesis (Abate-Shen, C. (2002) *Nat Rev Cancer* 2, 777-85). The homeobox superfamily of genes encodes transcription factors that are critical for normal development and are frequently inappropriately expressed in cancer (Abate-Shen, C. (2002) *Nat Rev Cancer* 2, 777-85; Ford, H. L. (1998) *Cell Biol Int* 22, 397-400). However, because few of their in vivo transcriptional targets have been identified, the molecular mechanisms by which they act or the relevance of their overexpression in cancer have been poorly understood to the present.

The Six family of homeobox genes has been implicated in the proliferation of progenitor populations prior to cell type specification (Li, X., Perissi, V., Liu, F., Rose, D. W. & Rosenfeld, M. G. (2002) *Science* 297, 1180-3; Kawakami, K., Sato, S., Ozaki, H. & Ikeda, K. (2000) *Bioessays* 22, 616-26; Relaix, F. & Buckingham, M. (1999) *Genes Dev* 13, 3171-8; Ozaki, H., Nakamura, K., Funahashi, J., Ikeda, K., Yamada, G., Tokano, H., Okamura, H. O., Kitamura, K., Muto, S., Kotaki, H., Sudo, K., Horai, R., Iwakura, Y. & Kawakami, K. (2004) *Development* 131, 551-62; Li, X., Oghi, K. A., Zhang, J., Krones, A., Bush, K. T., Glass, C. K., Nigam, S. K., Aggarwal, A. K., Maas, R., Rose, D. W. & Rosenfeld, M. G. (2003) *Nature* 426, 247-54; Zheng, W., Huang, L., Wei, Z. B., Silvius, D., Tang, B. & Xu, P. X. (2003) *Development* 130, 3989-4000; Zuber, M. E., Perron, M., Philpott, A., Bang, A. & Harris, W. A. (1999) *Cell* 98, 341-52; Goudreau, G., Petrou, P., Reneker, L. W., Graw, J., Loster, J. & Gruss, P. (2002) *Proc Natl Acad Sci USA* 99, 8719-24). Six6 represses the cyclin-dependent kinase inhibitor p27, thereby promoting progenitor cell proliferation in the pituitary gland and the retina (Li, X., Perissi, V., Liu, F., Rose, D. W. & Rosenfeld, M. G. (2002) *Science* 297, 1180-3). In Six1 knockout mice, multiple organs fail to develop properly due to an increase in apoptosis and a decrease in cellular proliferation (Ozaki, H., Nakamura, K., Funahashi, J., Ikeda, K., Yamada, G., Tokano, H., Okamura, H. O., Kitamura, K., Muto, S., Kotaki, H., Sudo, K., Horai, R., Iwakura, Y. & Kawakami, K. (2004) *Development* 131, 551-62; Li, X., Oghi, K. A., Zhang, J., Krones, A., Bush, K. T., Glass, C. K., Nigam, S. K., Aggarwal, A. K., Maas, R., Rose, D. W. & Rosenfeld, M. G. (2003) *Nature* 426, 247-54; Zheng, W., Huang, L., Wei, Z. B., Silvius, D., Tang, B. & Xu, P. X. (2003) *Development* 130, 3989-4000). Recently identified targets of Six1 include c-myc and Gdnf, both which are implicated in cell growth and proliferation (Li, X., Oghi, K. A., Zhang, J., Krones, A., Bush, K. T., Glass, C. K., Nigam, S. K., Aggarwal, A. K., Maas, R., Rose, D. W. & Rosenfeld, M. G. (2003) *Nature* 426, 247-54). The role of these genes in stimulating Six1-mediated proliferation has not been determined.

Several members of the Six family are implicated in the pathogenesis of human cancers (Laflamme, C., Filion, C., Bridge, J. A., Ladanyi, M., Goldring, M. B. & Labelle, Y. (2003) *Cancer Res* 63, 449-54; Winchester, C., Robertson, S., MacLeod, T., Johnson, K. & Thomas, M. (2000) *J Clin Pathol* 53, 212-7; Li, C. M., Guo, M., Borczuk, A., Powell, C. A., Wei, M., Thaker, H. M., Friedman, R., Klein, U. & Tycko, B. (2002) *Am J Pathol* 160, 2181-90; Khan, J., Bittner, M. L., Saal, L. H., Teichmann, U., Azorsa, D. O., Gooden, G. C., Pavan, W. J., Trent, J. M. & Meltzer, P. S. (1999) *Proc Natl Acad Sci USA* 96, 13264-9; Ford, H. L., Kabingu, E. N., Bump, E. A., Mutter, G. L. & Pardee, A. B. (1998) *Proc Natl Acad Sci USA* 95, 12608-13; Yu, Y., Khan, J., Khanna, C., Helman, L., Meltzer, P. S. & Merlino, G. (2004) *Nat Med* 10, 175-81). Due to their role in proliferation during normal development, it is possible that these genes, when aberrantly expressed, may play a role in the proliferative aspects of tumorigenesis. However, the molecular means by which the Six family members affect cancer has to the present remained unknown.

Six1 overexpression leads to an attenuation of the DNA damage-induced G2 checkpoint (Ford, H. L., Kabingu, E. N., Bump, E. A., Mutter, G. L. & Pardee, A. B. (1998) *Proc Natl Acad Sci USA* 95, 12608-13.). As well, Six1 overexpression occurs in 44% of primary breast cancers and 90% of metastatic lesions (Ford, H. L., Kabingu, E. N., Bump, E. A., Mutter, G. L. & Pardee, A. B. (1998) *Proc Natl Acad Sci USA* 95, 12608-13). Experiments conducted during the course of development of the present invention demonstrate additional roles of Six1 in the cell cycle, and identify a pathway by which Six1 influences cellular proliferation. By directly activating cyclin A1 transcription, Six1 sets in motion a means for proliferation in normal development that can be aberrantly utilized in tumorigenesis. Thus, the transcriptional activation of cyclin A1, a tissue-restricted cyclin that is expressed in the embryonic mammary gland but not in the differentiated-adult mammary gland, denotes the role of Six1 in both normal development and in cancer.

Members of the Six family are implicated in the proliferation of pluripotent precursor cells during development (Li, X., Perissi, V., Liu, F., Rose, D. W. & Rosenfeld, M. G. (2002) *Science* 297, 1180-3; Relaix, F. & Buckingham, M. (1999) *Genes Dev* 13, 3171-8; Ozaki, H., Nakamura, K., Funahashi, J., Ikeda, K., Yamada, G., Tokano, H., Okamura, H. O., Kitamura, K., Muto, S., Kotaki, H., Sudo, K., Horai, R., Iwakura, Y. & Kawakami, K. (2004) *Development* 131, 551-62; Li, X., Oghi, K. A., Zhang, J., Krones, A., Bush, K. T., Glass, C. K., Nigam, S. K., Aggarwal, A. K., Maas, R., Rose, D. W. & Rosenfeld, M. G. (2003) *Nature* 426, 247-54; Zheng, W., Huang, L., Wei, Z. B., Silvius, D., Tang, B. & Xu, P. X. (2003) *Development* 130, 3989-4000; Zuber, M. E., Perron, M., Philpott, A., Bang, A. & Harris, W. A. (1999) *Cell* 98, 341-52; Goudreau, G., Petrou, P., Reneker, L. W., Graw, J., Loster, J. & Gruss, P. (2002) *Proc Natl Acad Sci USA* 99, 8719-24). Loss-of-function of Six1 in mice results in a reduction in size or the absence of various organs, due to a decrease in proliferation and an increase in apoptosis (Ozaki, H., Nakamura, K., Funahashi, J., Ikeda, K., Yamada, G., Tokano, H., Okamura, H. O., Kitamura, K., Muto, S., Kotaki, H., Sudo, K., Horai, R., Iwakura, Y. & Kawakami, K. (2004) *Development* 131, 551-62; Li, X., Oghi, K. A., Zhang, J., Krones, A., Bush, K. T., Glass, C. K., Nigam, S. K., Aggarwal, A. K., Maas, R., Rose, D. W. & Rosenfeld, M. G. (2003) *Nature* 426, 247-54; Zheng, W., Huang, L., Wei, Z. B., Silvius, D., Tang, B. & Xu, P. X. (2003) *Development* 130, 3989-4000; Laclef, C., Hamard, G., Demignon, J., Souil, E., Houbron, C. & Maire, P. (2003) *Development* 130, 2239-52; Laclef, C., Souil, E., Demignon, J. & Maire, P. (2003) *Mech Dev* 120, 669-79). Experiments conducted during the course of development of the present invention show that Six1 enhances proliferation through the direct activation of the tissue-specific cyclin A1, and suggest that a developmental function of Six1 is to stimulate the proliferation of progenitor cells via cyclin A1. Six1 null animals express numerous defects (Laclef, C., Souil, E., Demignon, J. & Maire, P. (2003) *Mech Dev* 120, 669-79), whereas cyclin A1 knockout mice exhibit defects only in spermatogenesis (Liu, D., Matzuk, M. M., Sung, W. K., Guo, Q., Wang, P. & Wolgemuth, D. J. (1998) *Nat Genet* 20, 377-80). Therefore a role of cyclin A1 in the normal development of other organs in which it is expressed is apparently compensated by the presence of other cyclins. A similar phenomenon is observed in the cdk2 knockout mice, where a defect in spermatogenesis and oogenesis is observed, but the mice remain viable (Ortega, S., Prieto, I., Odajima, J., Martin, A., Dubus, P., Sotillo, R., Barbero, J. L., Malumbres, M. & Barbacid, M. (2003) *Nat Genet* 35, 25-31), and in cyclin E1/E2 null mice, in which some embryos that develop in the presence of a wild type placenta are viable (Geng, Y., Yu, Q., Sicinska, E., Das, M., Schneider, J. E., Bhattacharya, S., Rideout, W. M., Bronson, R. T., Gardner, H. & Sicinski, P. (2003) *Cell* 114, 431-43). As has been demonstrated for cyclins E1/E2, various cyclins and cdks may not be essential for cell cycle progression in normal development due to redundancy, but may still play a critical role in tumorigenesis (Geng, Y., Yu, Q., Sicinska, E., Das, M., Schneider, J. E., Bhattacharya, S., Rideout, W. M., Bronson, R. T., Gardner, H. & Sicinski, P. (2003) *Cell* 114, 431-43). Thus, the misexpression of Six1 in cancers causes an inappropriate re-activation of the cyclin A1-mediated proliferative pathway in adult somatic cells, promoting cell cycle progression and tumor growth. Together these findings provide a specific means for the expansion of cells both in development and cancer, which is likely used in organ systems in addition to the breast.

Six1 is expressed in a higher percentage of metastatic breast cancers than primary breast tumors (Ford, H. L., Kabingu, E. N., Bump, E. A., Mutter, G. L. & Pardee, A. B. (1998) *Proc Natl Acad Sci USA* 95, 12608-13), and it has recently been shown to regulate metastasis in a mouse rhabdomyosarcoma (RMS) model system (Yu, Y., Khan, J., Khanna, C., Helman, L., Meltzer, P. S. & Merlino, G. (2004) *Nat Med* 10, 175-81). Video microscopy studies of highly metastatic melanoma cells demonstrate that while 80% of cells injected into the liver survive and extravasate into the surrounding tissue, only 2.5% of the surviving cells will initiate cell division and form microscopic metastases, and only 1% will progress to form macroscopic tumors (Luzzi, K. J., MacDonald, I. C., Schmidt, E. E., Kerkvliet, N., Morris, V. L., Chambers, A. F. & Groom, A. C. (1998) *Am J Pathol* 153, 865-73). These studies suggest that the inhibition of apoptosis and the initiation of proliferation are important events in the development of metastases (Vander Griend, D. J. & Rinker-Schaeffer, C. W. (2004) *Sci STKE* 2004, pe3), both processes in which Six1 has been implicated. However, in addition to its effect on proliferation, Six1 was found to alter invasiveness in the RMS model (Yu, Y., Khan, J., Khanna, C., Helman, L., Meltzer, P. S. & Merlino, G. (2004) *Nat Med* 10, 175-81).

Most cancer therapies currently in use suffer from the fact that they do not exclusively target cancer cells, leading to unwanted and frequently severe side effects. In experiments conducted during the course of development of the present invention, elucidation of the Six1-cyclin A1 developmental pathway which is inappropriately activated in tumors, but relatively silent in most normal adult cells, yields an improved understanding of of tumorigenesis, and supports the development of novel, more tumor-specific cancer diagnostics and therapies.

The present invention is not limited to a particular mechanism. Indeed, an understanding of the mechanism is not necessary to practice the present invention. Nonetheless, it is contemplated that through the over expression of cyclin A1 activation potentiates breast cancer oncogenesis. Accordingly, in some embodiments, the present invention provides methods of preventing, diagnosing and treating cancer and related disease and conditions.

I. Cancer Therapy and Analysis

In some embodiments, the present invention provides therapies for treating and/or analyzing cancer. In some embodiments, methods inhibit Six1 or cyclin A1 function (e.g., by inhibiting the interaction of Six1 with cyclin A1). In other embodiments, methods inhibit function by modulating regulators or down stream signaling molecules of Six1 or cyclin A1. In some embodiments, additional inhibitors of Six1 or cyclin A1 function are identified using the drug screening applications disclosed herein.

A. Antisense and RNAi Therapies

In some embodiments, the present invention targets the expression of Six1 or cyclin A1 or signaling partners. For example, in some embodiments, the present invention employs compositions comprising oligomeric antisense compounds, particularly oligonucleotides, for use in modulating the function of nucleic acid molecules encoding Six1 or cyclin A1 or signaling partners thereof, ultimately modulating the amount of Six1 or cyclin A1 associated protein expressed. This is accomplished by providing antisense compounds (e.g., antisense oligonucleotides, siRNA, etc.) that specifically hybridize with one or more nucleic acids encoding Six1 or cyclin A1 or a signaling partner thereof. The specific hybridization of an oligomeric compound with its target nucleic acid interferes with the normal function of the nucleic acid.

i. RNA Interference (RNAi)

In some embodiments, RNAi is utilized to inhibit Six1 or cyclin A1 function. RNAi represents an evolutionary conserved cellular defense for controlling the expression of foreign genes in most eukaryotes, including humans. RNAi is typically triggered by double-stranded RNA (dsRNA) and causes sequence-specific mRNA degradation of single-stranded target RNAs homologous in response to dsRNA. The mediators of mRNA degradation are small interfering RNA duplexes (siRNAs), which are normally produced from long dsRNA by enzymatic cleavage in the cell. siRNAs are generally approximately twenty-one nucleotides in length (e.g. 21-23 nucleotides in length), and have a base-paired structure characterized by two nucleotide 3'-overhangs. Following the introduction of a small RNA, or RNAi, into the cell, it is believed the sequence is delivered to an enzyme complex called RISC(RNA-induced silencing complex). RISC recognizes the target and cleaves it with an endonuclease. It is noted that if larger RNA sequences are delivered to a cell, RNase III enzyme (Dicer) converts longer dsRNA into 21-23 nt ds siRNA fragments.

Chemically synthesized siRNAs have become powerful reagents for genome-wide analysis of mammalian gene function in cultured somatic cells. Beyond their value for validation of gene function, siRNAs also hold great potential as gene-specific therapeutic agents (Tuschl and Borkhardt, *Molecular Intervent.* 2002; 2(3):158-67, herein incorporated by reference).

The transfection of siRNAs into animal cells results in the potent, long-lasting post-transcriptional silencing of specific genes (Caplen et al, *Proc Natl Acad Sci U.S.A.* 2001; 98: 9742-7; Elbashir et al., *Nature.* 2001; 411:494-8; Elbashir et al., *Genes Dev.* 2001; 15: 188-200; and Elbashir et al., *EMBO J.* 2001; 20: 6877-88, all of which are herein incorporated by reference). Methods and compositions for performing RNAi with siRNAs are described, for example, in U.S. Pat. No. 6,506,559, herein incorporated by reference.

siRNAs are extraordinarily effective at lowering the amounts of targeted RNA, and by extension proteins, frequently to undetectable levels. The silencing effect can last several months, and is extraordinarily specific, because one nucleotide mismatch between the target RNA and the central region of the siRNA is frequently sufficient to prevent silencing (Brummelkamp et al, *Science* 2002; 296:550-3; and Holen et al, *Nucleic Acids Res* 2002; 30:1757-66, both of which are herein incorporated by reference).

ii. Antisense

In other embodiments, the present invention employs compositions comprising oligomeric antisense compounds, particularly oligonucleotides (e.g., those identified in the drug screening methods described below), for use in modulating the function of nucleic acid molecules encoding Six1 or cyclin A1, ultimately modulating the amount of Six1 or cyclin A1 expressed. This is accomplished by providing antisense compounds that specifically hybridize with one or more nucleic acids encoding Six1 or cyclin A1. The specific hybridization of an oligomeric compound with its target nucleic acid interferes with the normal function of the nucleic acid. This modulation of function of a target nucleic acid by compounds that specifically hybridize to it is generally referred to as "antisense." The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity that may be engaged in or facilitated by the RNA. The overall effect of such interference with target nucleic acid function is modulation of the expression of Six1 or cyclin A1. In the context of the present invention, "modulation" means either an increase (stimulation) or a decrease (inhibition) in the expression of a gene. For example, expression may be inhibited to potentially prevent tumor metastasis.

It is preferred to target specific nucleic acids for antisense. "Targeting" an antisense compound to a particular nucleic acid, in the context of the present invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding a Six1 or cyclin A1 protein. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). Eukaryotic and prokaryotic genes may have two or more alternative start codons, any one of which may be preferentially utilized for translation initiation in a particular cell type or tissue, or under a particular set of conditions. In the context of the present invention, "start codon" and "translation initiation codon" refer to the codon or codons that are used in vivo to initiate translation of an mRNA molecule transcribed from a gene encoding a tumor antigen of the present invention, regardless of the sequence(s) of such codons.

Translation termination codon (or "stop codon") of a gene may have one of three sequences (i.e., 5'-UAA, 5'-UAG and 5'-UGA; the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which refers to the region between the translation initiation codon and the translation termination codon, is also a region that may be targeted effectively. Other target regions include the 5' untranslated region (5' UTR), referring to the portion of an mRNA in the 5' direction from the translation initiation codon, and thus including nucleotides between the 5' cap site and the translation initiation codon of an mRNA or corresponding nucleotides on the gene, and the 3' untranslated region (3' UTR), referring to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The cap region may also be a preferred target region.

Although some eukaryotic mRNA transcripts are directly translated, many contain one or more regions, known as "introns," that are excised from a transcript before it is translated. The remaining (and therefore translated) regions are known as "exons" and are spliced together to form a continuous mRNA sequence. mRNA splice sites (i.e., intron-exon junctions) may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

In some embodiments, target sites for antisense inhibition are identified using commercially available software programs (e.g., Biognostik, Gottingen, Germany; SysArris Software, Bangalore, India; Antisense Research Group, University of Liverpool, Liverpool, England; GeneTrove, Carlsbad, Calif.). In other embodiments, target sites for antisense inhibition are identified using the accessible site method described in U.S. Patent WO0198537A2, herein incorporated by reference.

Once one or more target sites have been identified, oligonucleotides are chosen that are sufficiently complementary to the target (i.e., hybridize sufficiently well and with sufficient specificity) to give the desired effect. For example, in preferred embodiments of the present invention, antisense oligonucleotides are targeted to or near the start codon.

In the context of this invention, "hybridization," with respect to antisense compositions and methods, means hydrogen bonding, which may be Watson-Crick, Hoogsteen or reversed Hoogsteen hydrogen bonding, between complementary nucleoside or nucleotide bases. For example, adenine and thymine are complementary nucleobases that pair through the formation of hydrogen bonds. It is understood that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired (i.e., under physiological conditions in the case of in vivo assays or therapeutic treatment, and in the case of in vitro assays, under conditions in which the assays are performed).

Antisense compounds are commonly used as research reagents and diagnostics. For example, antisense oligonucleotides, which are able to inhibit gene expression with specificity, can be used to elucidate the function of particular genes. Antisense compounds are also used, for example, to distinguish between functions of various members of a biological pathway.

The specificity and sensitivity of antisense is also applied for therapeutic uses. For example, antisense oligonucleotides have been employed as therapeutic moieties in the treatment of disease states in animals and man. Antisense oligonucleotides have been safely and effectively administered to humans and numerous clinical trials are presently underway. It is thus established that oligonucleotides are useful therapeutic modalities that can be configured to be useful in treatment regimes for treatment of cells, tissues, and animals, especially humans.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 30 nucleobases (i.e., from about 8 to about 30 linked bases), although both longer and shorter sequences may find use with the present invention. Particularly preferred antisense compounds are antisense oligonucleotides, even more preferably those comprising from about 12 to about 25 nucleobases.

Specific examples of preferred antisense compounds useful with the present invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

In other preferred oligonucleotide mimetics, both the sugar and the internucleoside linkage (i.e., the backbone) of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science 254:1497 (1991).

Most preferred embodiments of the invention are oligonucleotides with phosphorothioate backbones and oligonucleosides with heteroatom backbones, and in particular —$CH_2$—, —NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$—, and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O-, S-, or N-alkyl; O-, S-, or N-alkenyl; O-, S- or N-alkynyl; or O-alkyl- O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., Helv. Chim. Acta 78:486 [1995]) i.e., an alkoxyalkoxy group. A further preferred modification includes 2'-dimethylaminooxyethoxy (i.e., a $O(CH_2)_2ON(CH_3)_2$ group), also known as 2'-DMAOE, and 2'-dimethylaminoethoxyethoxy (also known in the art as 2'-O-dimethylaminoethoxyethyl or 2'-DMAEOE), i.e., 2'-O—$CH_2$—O—$CH_2$—$N(CH_2)_2$.

Other preferred modifications include 2'-methoxy(2'-O—$CH_3$), 2'-aminopropoxy(2'-$OCH_2CH_2CH_2NH_2$) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2. degree ° C. and are presently preferred base substitutions, even more particularly when combined with 2'-O-methoxyethyl sugar modifications.

Another modification of the oligonucleotides of the present invention involves chemically linking to the oligonucleotide one or more moieties or conjugates that enhance the activity, cellular distribution or cellular uptake of the oligonucleotide. Such moieties include but are not limited to lipid moieties such as a cholesterol moiety, cholic acid, a thioether, (e.g., hexyl-5-tritylthiol), a thiocholesterol, an aliphatic chain, (e.g., dodecandiol or undecyl residues), a phospholipid, (e.g., di-hexadecyl-rac-glycerol or triethylammonium 1,2-di-O-hexadecyl-rac-glycero-3-H-phosphonate), a polyamine or a polyethylene glycol chain or adamantane acetic acid, a palmityl moiety, or an octadecylamine or hexylamino-carbonyl-oxycholesterol moiety.

One skilled in the relevant art knows well how to generate oligonucleotides containing the above-described modifications. The present invention is not limited to the antisense oligonucleotides described above. Any suitable modification or substitution may be utilized.

It is not necessary for all positions in a given compound to be uniformly modified, and in fact more than one of the aforementioned modifications may be incorporated in a single compound or even at a single nucleoside within an oligonucleotide. The present invention also includes antisense compounds that are chimeric compounds. "Chimeric" antisense compounds or "chimeras," in the context of the present invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNaseH is a cellular endonuclease that cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the present invention may be formed as composite structures of two or more oligonucleotides, modified oligonucleotides, oligonucleosides and/or oligonucleotide mimetics as described above.

The present invention also includes pharmaceutical compositions and formulations that include the antisense compounds of the present invention as described below.

B. Antibody Therapy

In other embodiments, the present invention provides antibodies that target Six1 or cyclin A1 or Six1 or cyclin A1 signal pathway components in cancer. Human anti-cyclin A1 antibodies may be obtained, for example, from Upstate USA, Inc., Charlottesville, Va. Human anti-Six1 antibodies may be obtained as described in Ford H. L., Landesman-Bollag E., Dacwag C. S., Stukenberg P. T., Pardee A. B. & Seldin D. C. (2000) *The Journal of Biological Chemistry* 275, 22245-22254, which is incorporated herein in its entirety. In preferred embodiments, the antibodies used for cancer therapy are humanized antibodies. Methods and compositions for generating antibodies are described below.

C. Small Molecule Drugs

In still further embodiments, the present invention provides drugs (e.g., small molecule drugs) that prevent metastasis by inhibiting the biological activity of Six1 or cyclin A1 or altering the biological activity of Six1 or cyclin A1 pathway components. In some embodiments, small molecule drugs are identified using the drug screening methods described below. In particularly preferred embodiments, the small molecule drugs of the present invention result in the inhibition or prevention of metastasis of cancer cells. In some embodiments, small molecule drugs are identified using the drug screening methods described below.

D. Genetic and Transplantation Therapies

In yet other embodiments, the present invention contemplates the use of any genetic manipulation for use in modulating the expression of Six1 or cyclin A1. Examples of genetic manipulation include, but are not limited to, delivery of inhibitors of Six1 or cyclin A1. (e.g., to cancer cells, tissues, or subjects). Delivery of nucleic acid construct to cells in vitro or in vivo may be conducted using any suitable method. A suitable method is one that introduces the nucleic acid construct into the cell such that the desired event occurs (e.g., expression of an antisense construct). For example, cells may be transfected ex vivo to decrease Six1 or cyclin A1 expression and the transfected cells may be transplanted to the site of a tumor.

Introduction of molecules carrying genetic information into cells is achieved by any of various methods including, but not limited to, directed injection of naked DNA constructs, bombardment with gold particles loaded with said constructs, and macromolecule mediated gene transfer using, for example, liposomes, biopolymers, and the like. Preferred methods use gene delivery vehicles derived from viruses, including, but not limited to, adenoviruses, retroviruses, vaccinia viruses, and adeno-associated viruses. Because of the higher efficiency as compared to retroviruses, vectors derived from adenoviruses are the preferred gene delivery vehicles for transferring nucleic acid molecules into host cells in vivo. Adenoviral vectors have been shown to provide very efficient in vivo gene transfer into a variety of solid tumors in animal models and into human solid tumor xenografts in immunedeficient mice. Examples of adenoviral vectors and methods for gene transfer are described in PCT publications WO 00/12738 and WO 00/09675 and U.S. Pat. Nos. 6,033,908, 6,019,978, 6,001,557, 5,994,132, 5,994,128, 5,994,106, 5,981,225, 5,885,808, 5,872,154, 5,830,730, and 5,824,544, each of which is herein incorporated by reference in its entirety.

Vectors may be administered to subject in a variety of ways. For example, in some embodiments of the present invention, vectors are administered into tumors or tissue associated with tumors using direct injection. In other embodiments, administration is via the blood or lymphatic circulation (See e.g., PCT publication 99/02685 herein incorporated by reference in its entirety). Exemplary dose levels of adenoviral vector are preferably $10^8$ to $10^{11}$ vector particles added to the perfusate.

E. Pharmaceutical Compositions

The present invention further provides pharmaceutical compositions (e.g., comprising the therapeutic compounds described above). The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product.

Agents that enhance uptake of oligonucleotides at the cellular level may also be added to the pharmaceutical and other compositions of the present invention. For example, cationic lipids, such as lipofectin (U.S. Pat. No. 5,705,188), cationic glycerol derivatives, and polycationic molecules, such as polylysine (WO 97/30731), also enhance the cellular uptake of oligonucleotides.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models or based on the examples described herein. In general, dosage is from 0.01 μg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the oligonucleotide is administered in maintenance doses, ranging from 0.01 μg to 100 g per kg of body weight, once or more daily, to once every 20 years.

F. Therapeutic Agents Combined or Co-Administered with Anti-Six1 or Anti-Cyclin A1 Compounds In some embodiments, the Six1 or cyclin A1 targeting compounds of the present invention are coadministered with additional therapeutic agents. A wide range of therapeutic agents find use with the present invention. Any therapeutic agent that can be co-administered with compounds that target Six1 or cyclin A1, or associated proteins.

Various classes of antineoplastic (e.g., anticancer) agents are contemplated for use in certain embodiments of the present invention. Anticancer agents suitable for use with the present invention include, but are not limited to, agents that induce apoptosis, agents that inhibit adenosine deaminase function, inhibit pyrimidine biosynthesis, inhibit purine ring biosynthesis, inhibit nucleotide interconversions, inhibit ribonucleotide reductase, inhibit thymidine monophosphate (TMP) synthesis, inhibit dihydrofolate reduction, inhibit DNA synthesis, form adducts with DNA, damage DNA, inhibit DNA repair, intercalate with DNA, deaminate asparagines, inhibit RNA synthesis, inhibit protein synthesis or stability, inhibit microtubule synthesis or function, and the like.

In some embodiments, exemplary anticancer agents suitable for use in compositions and methods of the present invention include, but are not limited to: 1) alkaloids, including microtubule inhibitors (e.g., vincristine, vinblastine, and vindesine, etc.), microtubule stabilizers (e.g., paclitaxel (TAXOL), and docetaxel, etc.), and chromatin function inhibitors, including topoisomerase inhibitors, such as epipodophyllotoxins (e.g., etoposide (VP-16), and teniposide (VM-26), etc.), and agents that target topoisomerase I (e.g., camptothecin and isirinotecan (CPT-11), etc.); 2) covalent DNA-binding agents (alkylating agents), including nitrogen mustards (e.g., mechlorethamine, chlorambucil, cyclophosphamide, ifosphamide, and busulfan (MYLERAN), etc.), nitrosoureas (e.g., carmustine, lomustine, and semustine, etc.), and other alkylating agents (e.g., dacarbazine, hydroxymethylmelamine, thiotepa, and mitomycin, etc.); 3) noncovalent DNA-binding agents (antitumor antibiotics), including nucleic acid inhibitors (e.g., dactinomycin (actinomycin D), etc.), anthracyclines (e.g., daunorubicin (daunomycin, and cerubidine), doxorubicin (adriamycin), and idarubicin (idamycin), etc.), anthracenediones (e.g., anthracycline analogues, such as mitoxantrone, etc.), bleomycins (BLENOXANE), etc., and plicamycin (mithramycin), etc.; 4) antimetabolites, including antifolates (e.g., methotrexate, FOLEX, and MEXATE, etc.), purine antimetabolites (e.g., 6-mercaptopurine (6-MP, PURINETHOL), 6-thioguanine (6-TG), azathioprine, acyclovir, ganciclovir, chlorodeoxyadenosine, 2-chlorodeoxyadenosine (CdA), and 2'-deoxycoformycin (pentostatin), etc.), pyrimidine antagonists (e.g., fluoropyrimidines (e.g., 5-fluorouracil (ADRUCIL), 5-fluorodeoxyuridine (FdUrd) (floxuridine)) etc.), and cytosine arabinosides (e.g., CYTOSAR (ara-C) and fludarabine, etc.); 5) enzymes, including L-asparaginase, and hydroxyurea, etc.; 6) hormones, including glucocorticoids, antiestrogens (e.g., tamoxifen, etc.), nonsteroidal antiandrogens (e.g., flutamide, etc.), and aromatase inhibitors (e.g., anastrozole (ARIMIDEX), etc.); 7) platinum compounds (e.g., cisplatin and carboplatin, etc.); 8) monoclonal antibodies conjugated with anticancer drugs, toxins, and/or radionuclides, etc.; 9) biological response modifiers (e.g., interferons (e.g., IFN-α, etc.) and interleukins (e.g., IL-2, etc.), etc.); 10) adoptive immunotherapy; 11) hematopoietic growth factors; 12) agents that induce tumor cell differentiation (e.g., all-trans-retinoic acid, etc.); 13) gene therapy techniques; 14) antisense therapy techniques; 15) tumor vaccines; 16) therapies directed against tumor metastases (e.g., batimastat, etc.); 17) angiogenesis inhibitors; 18) proteosome inhibitors (e.g., VELCADE); 19) inhibitors of acetylation and/or methylation (e.g., HDAC inhibitors); 20) modulators of NF kappa B; 21) inhibitors of cell cycle regulation (e.g., CDK inhibitors); 22) modulators of p53 protein function; and 23) radiation.

Any oncolytic agent that is routinely used in a cancer therapy context finds use in the compositions and methods of the present invention. For example, the U.S. Food and Drug Administration maintains a formulary of oncolytic agents approved for use in the United States. International counterpart agencies to the U.S.F.D.A. maintain similar formularies. Table 1 provides a list of exemplary antineoplastic agents approved for use in the U.S. Those skilled in the art will appreciate that the "product labels" required on all U.S. approved chemotherapeutics describe approved indications, dosing information, toxicity data, and the like, for the exemplary agents.

TABLE 1

| | | |
|---|---|---|
| Aldesleukin (des-alanyl-1, serine-125 human interleukin-2) | Proleukin | Chiron Corp., Emeryville, CA |
| Alemtuzumab (IgG1k anti CD52 antibody) | Campath | Millennium and ILEX Partners, LP, Cambridge, MA |

TABLE 1-continued

| | | |
|---|---|---|
| Alitretinoin (9-cis-retinoic acid) | Panretin | Ligand Pharmaceuticals, Inc., San Diego CA |
| Allopurinol (1,5-dihydro-4 H-pyrazolo[3,4-d]pyrimidin-4-one monosodium salt) | Zyloprim | GlaxoSmithKline, Research Triangle Park, NC |
| Altretamine (N,N,N',N',N'',N'',-hexamethyl-1,3,5-triazine-2,4,6-triamine) | Hexalen | US Bioscience, West Conshohocken, PA |
| Amifostine (ethanethiol, 2-[(3-aminopropyl)amino]-, dihydrogen phosphate (ester)) | Ethyol | US Bioscience |
| Anastrozole (1,3-Benzenediacetonitrile, a,a,a',a'-tetramethyl-5-(1H-1,2,4-triazol-1-ylmethyl)) | Arimidex | AstraZeneca Pharmaceuticals, LP, Wilmington, DE |
| Arsenic trioxide | Trisenox | Cell Therapeutic, Inc., Seattle, WA |
| Asparaginase (L-asparagine amidohydrolase, type EC-2) | Elspar | Merck & Co., Inc., Whitehouse Station, NJ |
| BCG Live (lyophilized preparation of an attenuated strain of *Mycobacterium bovis* (*Bacillus Calmette-Gukin* [BCG], substrain Montreal) | TICE BCG | Organon Teknika, Corp., Durham, NC |
| bexarotene capsules (4-[1-(5,6,7,8-tetrahydro-3,5,5,8,8-pentamethyl-2-napthalenyl) ethenyl] benzoic acid) | Targretin | Ligand Pharmaceuticals |
| bexarotene gel | Targretin | Ligand Pharmaceuticals |
| Bleomycin (cytotoxic glycopeptide antibiotics produced by *Streptomyces verticillus*; bleomycin $A_2$ and bleomycin $B_2$) | Blenoxane | Bristol-Myers Squibb Co., NY, NY |
| Capecitabine (5'-deoxy-5-fluoro-N-[(pentyloxy)carbonyl]-cytidine) | Xeloda | Roche |
| Carboplatin (platinum, diammine [1,1-cyclobutanedicarboxylato(2-)-0,0']-,(SP-4-2)) | Paraplatin | Bristol-Myers Squibb |
| Carmustine (1,3-bis(2-chloroethyl)-1-nitrosourea) | BCNU, BiCNU | Bristol-Myers Squibb |
| Carmustine with Polifeprosan 20 Implant | Gliadel Wafer | Guilford Pharmaceuticals, Inc., Baltimore, MD |
| Celecoxib (as 4-[5-(4-methylphenyl)-3-(trifluoromethyl)-1H-pyrazol-1-yl] benzenesulfonamide) | Celebrex | Searle Pharmaceuticals, England |
| Chlorambucil (4-[bis(2chlorethyl)amino]benzenebutanoic acid) | Leukeran | GlaxoSmithKline |
| Cisplatin ($PtCl_2H_6N_2$) | Platinol | Bristol-Myers Squibb |
| Cladribine (2-chloro-2'-deoxy-b-D-adenosine) | Leustatin, 2-CdA | R. W. Johnson Pharmaceutical Research Institute, Raritan, NJ |
| Cyclophosphamide (2-[bis(2-chloroethyl)amino] tetrahydro-2H-13,2-oxazaphosphorine 2-oxide monohydrate) | Cytoxan, Neosar | Bristol-Myers Squibb |
| Cytarabine (1-b-D-Arabinofuranosylcytosine, $C_9H_{13}N_3O_5$) | Cytosar-U | Pharmacia & Upjohn Company |
| cytarabine liposomal | DepoCyt | Skye Pharmaceuticals, Inc., San Diego, CA |
| Dacarbazine (5-(3,3-dimethyl-1-triazeno)-imidazole-4-carboxamide (DTIC)) | DTIC-Dome | Bayer AG, Leverkusen, Germany |
| Dactinomycin, actinomycin D (actinomycin produced by *Streptomyces parvullus*, $C_{62}H_{86}N_{12}O_{16}$) | Cosmegen | Merck |
| Darbepoetin alfa (recombinant peptide) | Aranesp | Amgen, Inc., Thousand Oaks, CA |
| daunorubicin liposomal ((8S-cis)-8-acetyl-10-[(3-amino-2,3,6-trideoxy-á-L-lyxo-hexopyranosyl)oxy]-7,8,9,10-tetrahydro-6,8,11-trihydroxy-1-methoxy-5,12-naphthacenedione hydrochloride) | DanuoXome | Nexstar Pharmaceuticals, Inc., Boulder, CO |
| Daunorubicin HCl, daunomycin ((1S,3S)-3-Acetyl-1,2,3,4,6,11-hexahydro-3,5,12-trihydroxy-10-methoxy-6,11-dioxo-1- | Cerubidine | Wyeth Ayerst, Madison, NJ |

TABLE 1-continued

| | | |
|---|---|---|
| naphthacenyl 3-amino-2,3,6-trideoxy-(alpha)-L-lyxo-hexopyranoside hydrochloride) | | |
| Denileukin diftitox (recombinant peptide) | Ontak | Seragen, Inc., Hopkinton, MA |
| Dexrazoxane ((S)-4,4'-(1-methyl-1,2-ethanediyl)bis-2,6-piperazinedione) | Zinecard | Pharmacia & Upjohn Company |
| Docetaxel ((2R,3S)-N-carboxy-3-phenylisoserine, N-tert-butyl ester, 13-ester with 5b-20-epoxy-12a,4,7b,10b,13a-hexahydroxytax-11-en-9-one 4-acetate 2-benzoate, trihydrate) | Taxotere | Aventis Pharmaceuticals, Inc., Bridgewater, NJ |
| Doxorubicin HCl (8S,10S)-10-[(3-amino-2,3,6-trideoxy-a-L-lyxo-hexopyranosyl)oxy]-8-glycolyl-7,8,9,10-tetrahydro-6,8,11-trihydroxy-1-methoxy-5,12-naphthacenedione hydrochloride) | Adriamycin, Rubex | Pharmacia & Upjohn Company |
| doxorubicin | Adriamycin PFS Intravenous injection | Pharmacia & Upjohn Company |
| doxorubicin liposomal | Doxil | Sequus Pharmaceuticals, Inc., Menlo park, CA |
| dromostanolone propionate (17b-Hydroxy-2a-methyl-5a-androstan-3-one propionate) | Dromostanolone | Eli Lilly & Company, Indianapolis, IN |
| dromostanolone propionate | Masterone injection | Syntex, Corp., Palo Alto, CA |
| Elliott's B Solution | Elliott's B Solution | Orphan Medical, Inc |
| Epirubicin ((8S-cis)-10-[(3-amino-2,3,6-trideoxy-a-L-arabino-hexopyranosyl)oxy]-7,8,9,10-tetrahydro-6,8,11-trihydroxy-8-(hydroxyacetyl)-1-methoxy-5,12-naphthacenedione hydrochloride) | Ellence | Pharmacia & Upjohn Company |
| Epoetin alfa (recombinant peptide) | Epogen | Amgen, Inc |
| Estramustine (estra-1,3,5(10)-triene-3,17-diol(17(beta))-, 3-[bis(2-chloroethyl)carbamate] 17-(dihydrogen phosphate), disodium salt, monohydrate, or estradiol 3-[bis(2-chloroethyl)carbamate] 17-(dihydrogen phosphate), disodium salt, monohydrate) | Emcyt | Pharmacia & Upjohn Company |
| Etoposide phosphate (4'-Demethylepipodophyllotoxin 9-[4,6-O-(R)-ethylidene-(beta)-D-glucopyranoside], 4'-(dihydrogen phosphate)) | Etopophos | Bristol-Myers Squibb |
| etoposide, VP-16 (4'-demethylepipodophyllotoxin 9-[4,6-0-(R)-ethylidene-(beta)-D-glucopyranoside]) | Vepesid | Bristol-Myers Squibb |
| Exemestane (6-methylenandrosta-1,4-diene-3,17-dione) | Aromasin | Pharmacia & Upjohn Company |
| Filgrastim (r-metHuG-CSF) | Neupogen | Amgen, Inc |
| floxuridine (intraarterial) (2'-deoxy-5-fluorouridine) | FUDR | Roche |
| Fludarabine (fluorinated nucleotide analog of the antiviral agent vidarabine, 9-b-D-arabinofuranosyladenine (ara-A)) | Fludara | Berlex Laboratories, Inc., Cedar Knolls, NJ |
| Fluorouracil, 5-FU (5-fluoro-2,4(1H,3H)-pyrimidinedione) | Adrucil | ICN Pharmaceuticals, Inc., Humacao, Puerto Rico |
| Fulvestrant (7-alpha-[9-(4,4,5,5,5-penta fluoropentylsulphinyl) nonyl]estra-1,3,5-(10)-triene-3,17-beta-diol) | Faslodex | IPR Pharmaceuticals, Guayama, Puerto Rico |
| Gemcitabine (2'-deoxy-2',2'-difluorocytidine monohydrochloride (b-isomer)) | Gemzar | Eli Lilly |
| Gemtuzumab Ozogamicin (anti-CD33 hP67.6) | Mylotarg | Wyeth Ayerst |
| Goserelin acetate (acetate salt of [D-Ser(But)$^6$,Azgly$^{10}$]LHRH; pyro-Glu-His-Trp-Ser-Tyr-D-Ser(But)-Leu-Arg-Pro-Azgly-NH2 acetate [$C_{59}H_{84}N_{18}O_{14}$·($C_2H_4O_2$)$_x$ | Zoladex Implant | AstraZeneca Pharmaceuticals |
| Hydroxyurea | Hydrea | Bristol-Myers Squibb |
| Ibritumomab Tiuxetan (immunoconjugate resulting from a thiourea covalent bond between the monoclonal antibody | Zevalin | Biogen IDEC, Inc., Cambridge MA |

TABLE 1-continued

| | | |
|---|---|---|
| Ibritumomab and the linker-chelator tiuxetan [N-[2-bis(carboxymethyl)amino]-3-(p-isothiocyanatophenyl)-propyl]-[N-[2-bis(carboxymethyl)amino]-2-(methyl)-ethyl]glycine) | | |
| Idarubicin (5,12-Naphthacenedione, 9-acetyl-7-[(3-amino-2,3,6-trideoxy-(alpha)-L-lyxo-hexopyranosyl)oxy]-7,8,9,10-tetrahydro-6,9,11-trihydroxyhydrochloride, (7S-cis)) | Idamycin | Pharmacia & Upjohn Company |
| Ifosfamide (3-(2-chloroethyl)-2-[(2-chloroethyl)amino]tetrahydro-2H-1,3,2-oxazaphosphorine 2-oxide) | IFEX | Bristol-Myers Squibb |
| Imatinib Mesilate (4-[(4-Methyl-1-piperazinyl)methyl]-N-[4-methyl-3-[[4-(3-pyridinyl)-2-pyrimidinyl]amino]-phenyl]benzamide methanesulfonate) | Gleevec | Novartis AG, Basel, Switzerland |
| Interferon alfa-2a (recombinant peptide) | Roferon-A | Hoffmann-La Roche, Inc., Nutley, NJ |
| Interferon alfa-2b (recombinant peptide) | Intron A (Lyophilized Betaseron) | Schering AG, Berlin, Germany |
| Irinotecan HCl ((4S)-4,11-diethyl-4-hydroxy-9-[(4-piperi-dinopiperidino)carbonyloxy]-1H-pyrano[3',4':6,7] indolizino[1,2-b] quinoline-3,14(4H, 12H) dione hydrochloride trihydrate) | Camptosar | Pharmacia & Upjohn Company |
| Letrozole (4,4'-(1H-1,2,4-Triazol-1-ylmethylene) dibenzonitrile) | Femara | Novartis |
| Leucovorin (L-Glutamic acid, N[4[[(2amino-5-formyl-1,4,5,6,7,8 hexahydro4oxo6-pteridinyl)methyl]amino]benzoyl], calcium salt (1:1)) | Wellcovorin, Leucovorin | Immunex, Corp., Seattle, WA |
| Levamisole HCl ((-)-(S)-2,3,5,6-tetrahydro-6-phenylimidazo [2,1-b] thiazole monohydrochloride $C_{11}H_{12}N_2S \cdot HCl$) | Ergamisol | Janssen Research Foundation, Titusville, NJ |
| Lomustine (1-(2-chloro-ethyl)-3-cyclohexyl-1-nitrosourea) | CeeNU | Bristol-Myers Squibb |
| Meclorethamine, nitrogen mustard (2-chloro-N-(2-chloroethyl)-N-methylethanamine hydrochloride) | Mustargen | Merck |
| Megestrol acetate 17α(acetyloxy)-6-methylpregna-4,6-diene-3,20-dione | Megace | Bristol-Myers Squibb |
| Melphalan, L-PAM (4-[bis(2-chloroethyl) amino]-L-phenylalanine) | Alkeran | GlaxoSmithKline |
| Mercaptopurine, 6-MP (1,7-dihydro-6 H-purine-6-thione monohydrate) | Purinethol | GlaxoSmithKline |
| Mesna (sodium 2-mercaptoethane sulfonate) | Mesnex | Asta Medica |
| Methotrexate (N-[4-[[(2,4-diamino-6-pteridinyl)methyl]methylamino]benzoyl]-L-glutamic acid) | Methotrexate | Lederle Laboratories |
| Methoxsalen (9-methoxy-7H-furo[3,2-g][1]-benzopyran-7-one) | Uvadex | Therakos, Inc., Way Exton, Pa |
| Mitomycin C | Mutamycin | Bristol-Myers Squibb |
| mitomycin C | Mitozytrex | SuperGen, Inc., Dublin, CA |
| Mitotane (1,1-dichloro-2-(o-chlorophenyl)-2-(p-chlorophenyl) ethane) | Lysodren | Bristol-Myers Squibb |
| Mitoxantrone (1,4-dihydroxy-5,8-bis[[2-[(2-hydroxyethyl)amino]ethyl]amino]-9,10-anthracenedione dihydrochloride) | Novantrone | Immunex Corporation |
| Nandrolone phenpropionate | Durabolin-50 | Organon, Inc., West Orange, NJ |
| Nofetumomab | Verluma | Boehringer Ingelheim Pharma KG, Germany |
| Oprelvekin (IL-11) | Neumega | Genetics Institute, Inc., Alexandria, VA |
| Oxaliplatin (cis-[(1R,2R)-1,2-cyclohexanediamine-N,N'] [oxalato(2-)-O,O'] platinum) | Eloxatin | Sanofi Synthelabo, Inc., NY, NY |

TABLE 1-continued

| | | |
|---|---|---|
| Paclitaxel (5β, 20-Epoxy-1,2a, 4,7β, 10β, 13a-hexahydroxytax-11-en-9-one 4,10-diacetate 2-benzoate 13-ester with (2R,3S)-N-benzoyl-3-phenylisoserine) | TAXOL | Bristol-Myers Squibb |
| Pamidronate (phosphonic acid (3-amino-1-hydroxypropylidene) bis-, disodium salt, pentahydrate, (APD)) | Aredia | Novartis |
| Pegademase ((monomethoxypolyethylene glycol succinimidyl) 11-17-adenosine deaminase) | Adagen (Pegademase Bovine) | Enzon Pharmaceuticals, Inc., Bridgewater, NJ |
| Pegaspargase (monomethoxypolyethylene glycol succinimidyl L-asparaginase) | Oncaspar | Enzon |
| Pegfilgrastim (covalent conjugate of recombinant methionyl human G-CSF (Filgrastim) and monomethoxypolyethylene glycol) | Neulasta | Amgen, Inc |
| Pentostatin | Nipent | Parke-Davis Pharmaceutical Co., Rockville, MD |
| Pipobroman | Vercyte | Abbott Laboratories, Abbott Park, IL |
| Plicamycin, Mithramycin (antibiotic produced by *Streptomyces plicatus*) | Mithracin | Pfizer, Inc., NY, NY |
| Porfimer sodium | Photofrin | QLT Phototherapeutics, Inc., Vancouver, Canada |
| Procarbazine (N-isopropyl-μ-(2-methylhydrazino)-p-toluamide monohydrochloride) | Matulane | Sigma Tau Pharmaceuticals, Inc., Gaithersburg, MD |
| Quinacrine (6-chloro-9-(1-methyl-4-diethyl-amine) butylamino-2-methoxyacridine) | Atabrine | Abbott Labs |
| Rasburicase (recombinant peptide) | Elitek | Sanofi-Synthelabo, Inc., |
| Rituximab (recombinant anti-CD20 antibody) | Rituxan | Genentech, Inc., South San Francisco, CA |
| Sargramostim (recombinant peptide) | Prokine | Immunex Corp |
| Streptozocin (streptozocin 2-deoxy-2-[[(methylnitrosoamino)carbonyl]amino]-a(and b)-D-glucopyranose and 220 mg citric acid anhydrous) | Zanosar | Pharmacia & Upjohn Company |
| Talc ($Mg_3Si_4O_{10}(OH)_2$) | Sclerosol | Bryan, Corp., Woburn, MA |
| Tamoxifen ((Z)2-[4-(1,2-diphenyl-1-butenyl) phenoxy]-N,N-dimethylethanamine 2-hydroxy-1,2,3-propanetricarboxylate (1:1)) | Nolvadex | AstraZeneca Pharmaceuticals |
| Temozolomide (3,4-dihydro-3-methyl-4-oxoimidazo[5,1-d]-as-tetrazine-8-carboxamide) | Temodar | Schering |
| teniposide, VM-26 (4'-demethylepipodophyllotoxin 9-[4,6-0-(R)-2-thenylidene-(beta)-D-glucopyranoside]) | Vumon | Bristol-Myers Squibb |
| Testolactone (13-hydroxy-3-oxo-13,17-secoandrosta-1,4-dien-17-oic acid [dgr]-lactone) | Teslac | Bristol-Myers Squibb |
| Thioguanine, 6-TG (2-amino-1,7-dihydro-6 H-purine-6-thione) | Thioguanine | GlaxoSmithKline |
| Thiotepa (Aziridine, 1,1',1''-phosphinothioylidynetris-, or Tris (1-aziridinyl) phosphine sulfide) | Thioplex | Immunex Corporation |
| Topotecan HCl ((S)-10-[(dimethylamino) methyl]-4-ethyl-4,9-dihydroxy-1H-pyrano[3',4': 6,7] indolizino [1,2-b] quinoline-3,14-(4H,12H)-dione monohydrochloride) | Hycamtin | GlaxoSmithKline |
| Toremifene (2-(p-[(Z)-4-chloro-1,2-diphenyl-1-butenyl]-phenoxy)-N,N-dimethylethylamine citrate (1:1)) | Fareston | Roberts Pharmaceutical Corp., Eatontown, NJ |
| Tositumomab, I 131 Tositumomab (recombinant murine immunotherapeutic monoclonal $IgG_{2a}$ lambda anti-CD20 antibody (I 131 is a radioimmunotherapeutic antibody)) | Bexxar | Corixa Corp., Seattle, WA |

TABLE 1-continued

| | | |
|---|---|---|
| Trastuzumab (recombinant monoclonal IgG$_1$ kappa anti-HER2 antibody) | Herceptin | Genentech, Inc |
| Tretinoin, ATRA (all-trans retinoic acid) | Vesanoid | Roche |
| Uracil Mustard | Uracil Mustard Capsules | Roberts Labs |
| Valrubicin, N-trifluoroacetyladriamycin-14-valerate ((2S-cis)-2-[1,2,3,4,6,11-hexahydro-2,5,12-trihydroxy-7 methoxy-6,11-dioxo-[[4 2,3,6-trideoxy-3-[(trifluoroacetyl)-amino-α-L-lyxo-hexopyranosyl]oxyl]-2-naphthacenyl]-2-oxoethyl pentanoate) | Valstar | Anthra --> Medeva |
| Vinblastine, Leurocristine ($C_{46}H_{56}N_4O_{10} \cdot H_2SO_4$) | Velban | Eli Lilly |
| Vincristine ($C_{46}H_{56}N_4O_{10} \cdot H_2SO_4$) | Oncovin | Eli Lilly |
| Vinorelbine (3',4'-didehydro-4'-deoxy-C'-norvincaleukoblastine [R-(R*,R*)-2,3-dihydroxybutanedioate (1:2)(salt)]) | Navelbine | GlaxoSmithKline |
| Zoledronate, Zoledronic acid ((1-Hydroxy-2-imidazol-1-yl-phosphonoethyl) phosphonic acid monohydrate) | Zometa | Novartis |

II. Antibodies

The present invention provides isolated antibodies. In preferred embodiments, the present invention provides monoclonal antibodies that specifically bind to an isolated polypeptide comprised of at least five amino acid residues of Six1 or cyclin A1. These antibodies find use in the diagnostic methods described herein. In some embodiments, antibodies also find use in research applications, drug screening, and therapeutic applications (e.g., antibodies directed to factors that influence Six1 or cyclin A1 signaling).

An antibody against a protein of the present invention may be any monoclonal or polyclonal antibody, as long as it can recognize the protein. Antibodies can be produced by using a protein of the present invention as the antigen according to a conventional antibody or antiserum preparation process.

The present invention contemplates the use of both monoclonal and polyclonal antibodies. Any suitable method may be used to generate the antibodies used in the methods and compositions of the present invention, including but not limited to, those disclosed herein. For example, for preparation of a monoclonal antibody, protein, as such, or together with a suitable carrier or diluent is administered to an animal (e.g., a mammal) under conditions that permit the production of antibodies. For enhancing the antibody production capability, complete or incomplete Freund's adjuvant may be administered. Normally, the protein is administered once every 2 weeks to 6 weeks, in total, about 2 times to about 10 times. Animals suitable for use in such methods include, but are not limited to, primates, rabbits, dogs, guinea pigs, mice, rats, sheep, goats, etc.

For preparing monoclonal antibody-producing cells, an individual animal whose antibody titer has been confirmed (e.g., a mouse) is selected, and 2 days to 5 days after the final immunization, its spleen or lymph node is harvested and antibody-producing cells contained therein are fused with myeloma cells to prepare the desired monoclonal antibody producer hybridoma. Measurement of the antibody titer in antiserum can be carried out, for example, by reacting the labeled protein, as described hereinafter, and antiserum and then measuring the activity of the labeling agent bound to the antibody. The cell fusion can be carried out according to known methods, for example, the method described by Koehler and Milstein (Nature 256:495 [1975]). As a fusion promoter, for example, polyethylene glycol (PEG) or Sendai virus (HVJ), preferably PEG is used.

Examples of myeloma cells include NS-1, P3U1, SP2/0, AP-1 and the like. The proportion of the number of antibody producer cells (spleen cells) and the number of myeloma cells to be used is preferably about 1:1 to about 20:1. PEG (preferably PEG 1000-PEG 6000) is preferably added in concentration of about 10% to about 80%. Cell fusion can be carried out efficiently by incubating a mixture of both cells at about 20° C. to about 40° C., preferably about 30° C. to about 37° C. for about 1 minute to 10 minutes.

Various methods may be used for screening for a hybridoma producing the antibody (e.g., against Six1 or cyclin A1). For example, where a supernatant of the hybridoma is added to a solid phase (e.g., microplate) to which antibody is adsorbed directly or together with a carrier and then an anti-immunoglobulin antibody (if mouse cells are used in cell fusion, anti-mouse immunoglobulin antibody is used) or Protein A labeled with a radioactive substance or an enzyme is added to detect the monoclonal antibody against the protein bound to the solid phase. Alternately, a supernatant of the hybridoma is added to a solid phase to which an anti-immunoglobulin antibody or Protein A is adsorbed and then the protein labeled with a radioactive substance or an enzyme is added to detect the monoclonal antibody against the protein bound to the solid phase.

Selection of the monoclonal antibody can be carried out according to any known method or its modification. Normally, a medium for animal cells to which HAT (hypoxanthine, aminopterin, thymidine) are added is employed. Any selection and growth medium can be employed as long as the hybridoma can grow. For example, RPMI 1640 medium containing 1% to 20%, preferably 10% to 20% fetal bovine serum, GIT medium containing 1% to 10% fetal bovine serum, a serum free medium for cultivation of a hybridoma (SFM-101, Nissui Seiyaku) and the like can be used. Normally, the cultivation is carried out at 20° C. to 40° C., preferably 37° C. for about 5 days to 3 weeks, preferably 1 week to 2 weeks under about 5% $CO_2$ gas. The antibody titer of the supernatant of a hybridoma culture can be measured according to the same manner as described above with respect to the antibody titer of the anti-protein in the antiserum.

Separation and purification of a monoclonal antibody (e.g., against Six1 or cyclin A1 can be carried out according to the same manner as those of conventional polyclonal antibodies such as separation and purification of immunoglobulins, for example, salting-out, alcoholic precipitation, isoelectric point precipitation, electrophoresis, adsorption and desorption with ion exchangers (e.g., DEAE), ultracentrifugation, gel filtration, or a specific purification method wherein only an antibody is collected with an active adsorbent such as an antigen-binding solid phase, Protein A or Protein G and dissociating the binding to obtain the antibody.

Polyclonal antibodies may be prepared by any known method or modifications of these methods including obtaining antibodies from patients. For example, a complex of an immunogen (an antigen against the protein) and a carrier protein is prepared and an animal is immunized by the complex according to the same manner as that described with respect to the above monoclonal antibody preparation. A material containing the antibody against is recovered from the immunized animal and the antibody is separated and purified.

As to the complex of the immunogen and the carrier protein to be used for immunization of an animal, any carrier protein and any mixing proportion of the carrier and a hapten can be employed as long as an antibody against the hapten, which is crosslinked on the carrier and used for immunization, is produced efficiently. For example, bovine serum albumin, bovine cycloglobulin, keyhole limpet hemocyanin, etc. may be coupled to an hapten in a weight ratio of about 0.1 part to about 20 parts, preferably, about 1 part to about 5 parts per 1 part of the hapten.

In addition, various condensing agents can be used for coupling of a hapten and a carrier. For example, glutaraldehyde, carbodiimide, maleimide activated ester, activated ester reagents containing thiol group or dithiopyridyl group, and the like find use with the present invention. The condensation product as such or together with a suitable carrier or diluent is administered to a site of an animal that permits the antibody production. For enhancing the antibody production capability, complete or incomplete Freund's adjuvant may be administered. Normally, the protein is administered once every 2 weeks to 6 weeks, in total, about 3 times to about 10 times.

The polyclonal antibody is recovered from blood, ascites and the like, of an animal immunized by the above method. The antibody titer in the antiserum can be measured according to the same manner as that described above with respect to the supernatant of the hybridoma culture. Separation and purification of the antibody can be carried out according to the same separation and purification method of immunoglobulin as that described with respect to the above monoclonal antibody.

The protein used herein as the immunogen is not limited to any particular type of immunogen. For example, Six1 or cyclin A1 protein (further including a gene having a nucleotide sequence partly altered) can be used as the immunogen. Further, fragments of the protein may be used. Fragments may be obtained by any methods including, but not limited to expressing a fragment of the gene, enzymatic processing of the protein, chemical synthesis, and the like.

In some embodiments, antibodies (e.g., monoclonal antibodies) are humanized. Such humanized antibodies find particular use in the cancer immunotherapies described below. Humanized antibodies are altered in order to make them less immunogenic to humans, e.g., by constructing chimeric antibodies in which a mouse antigen-binding variable domain is coupled to a human constant domain. Humanized antibodies are typically human antibodies in which some CDR residues and possibly some FR residues are substituted by residues from analogous sites in rodent antibodies. Methods for humanizing antibodies are well known in the art and include but are not limited to, those disclosed in U.S. Pat. Nos. 6,054,297, 4,816,567, 6,180,377, 5,871,907, 5,585,089, and 6,180,370, each of which is herein incorporated by reference.

III. Drug Screening

In some embodiments, the present invention provides drug screening assays (e.g., to screen for anticancer drugs). In some embodiments, the screening methods of the present invention utilize Six1 or cyclin A1. For example, in some embodiments, the present invention provides methods of screening for compounds that alter (e.g., decrease) the expression of Six1 or cyclin A1. In other embodiments, candidate compounds are antisense agents (e.g., oligonucleotides) directed against Six1 or cyclin A1. In still further embodiments, candidate compounds are small molecules that inhibit the activity of Six1 or cyclin A1.

In one screening method, candidate compounds are evaluated for their ability to alter (e.g., decrease) Six1 or cyclin A1 expression by contacting a compound with a cell expressing Six1 or cyclin A1 and then assaying for the effect of the candidate compounds on expression. In some embodiments, the effect of candidate compounds on expression of Six1 or cyclin A1 is assayed for by detecting the level of Six1 or cyclin A1 mRNA expressed by the cell. mRNA expression can be detected by any suitable method, including but not limited to, those disclosed herein.

In other embodiments, the effect of candidate compounds is assayed by measuring the level of Six1 or cyclin A1 expression. The level of polypeptide expressed can be measured using any suitable method, including but not limited to, those disclosed herein or by monitoring a phenotype (e.g., prevention of metastasis).

In some embodiments, in vitro drug screens are performed using purified wild type or dominant active Six1 or cyclin A1 and binding partners thereof. Compounds are screened for their ability to interact with Six1 or cyclin A1 proteins and inhibit Six1 or cyclin A1 function or the interaction of Six1 or cyclin A1 with binding partners. In some embodiments, cadherins or other binding partners are immobilized to facilitate separation of complexed from uncomplexed forms of one or both of the proteins, as well as to accommodate automation of the assay. Binding of a test compound to Six1 or cyclin A1 signaling proteins is accomplished in any vessel suitable for containing the reactants. Examples of such vessels include microtitre plates, test tubes, and microcentrifuge tubes. In one embodiment, a fusion protein can be provided which adds a domain that allows one or both of the proteins to be bound to a matrix. For example, glutathione-S-transferase/AIP-6 fusion proteins or glutathione-5-transferase/target fusion proteins can be adsorbed onto glutathione sepharose beads (Sigma Chemical; St. Louis, Mo.) or glutathione derivatized microtitre plates, which are then combined with the test compound or the test compound and the non-adsorbed protein, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly. Alternatively, the complexes can be dissociated from the matrix, and the level of protein binding or activity determined using standard techniques.

Other techniques for immobilizing proteins on matrices can also be used in the screening assays of the invention. For example, downstream Six1 or cyclin A1 signaling proteins or other protein known to interact with or modulate signaling by Six1 or cyclin A1 can be immobilized utilizing conjugation of biotin and streptavidin. Biotinylated proteins are prepared from biotin-NHS (N-hydroxy-succinimide) using techniques well known in the art (e.g., biotinylation kit, Pierce Chemicals; Rockford, Ill.), and immobilized in the wells of streptavidin-coated 96 well plates (Pierce Chemical). Alternatively, antibodies reactive with Six1 or cyclin A1 signaling proteins but which do not interfere with binding of the protein to test compounds can be derivatized to the wells of the plate, and unbound protein trapped in the wells by antibody conjugation. Methods for detecting such complexes, in addition to those described above for the GST-immobilized Six1 or cyclin A1 signaling proteins, as well as enzyme-linked assays that rely on detecting an enzymatic activity associated with Six1 or cyclin A1 signaling.

In other embodiments, competitive drug screening assays in which neutralizing antibodies capable of binding Six1 or cyclin A1 specifically compete with a test compound for binding to Six1 or cyclin A1 are utilized. In this manner, the antibodies can be used to detect the presence of any compound that shares one or more antigenic determinants with Six1 or cyclin A1.

In still further embodiments, transgenic animals having an altered (e.g., inactivated or overexpressed) Six1 or cyclin A1 gene are utilized in drug screening applications. For example, in some embodiments, compounds are screened for their ability to reduce cancer in Six1 or cyclin A1 mice.

The test compounds of the present invention can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., *J. Med. Chem.* 37: 2678-85 [1994]); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al., *Proc. Natl. Acad. Sci. U.S.A.* 90:6909 [1993]; Erb et al., *Proc. Nat. Acad. Sci. USA* 91:11422 [1994]; Zuckermann et al., *J. Med. Chem.* 37:2678 [1994]; Cho et al., *Science* 261:1303 [1993]; Carrell et al., Angew. *Chem. Int. Ed. Engl.* 33.2059 [1994]; Carell et al., Angew. *Chem. Int. Ed. Engl.* 33:2061 [1994]; and Gallop et al., *J. Med. Chem.* 37:1233 [1994].

Libraries of compounds may be presented in solution (e.g., Houghten, *Biotechniques* 13:412-421 [1992]), or on beads (Lam, *Nature* 354:82-84 [1991]), chips (Fodor, *Nature* 364: 555-556 [1993]), bacteria or spores (U.S. Pat. No. 5,223,409; herein incorporated by reference), plasmids (Cull et al., *Proc. Nad. Acad. Sci. USA* 89:18651869 [1992]) or on phage (Scott and Smith, *Science* 249:386-390 [1990]; Devlin *Science* 249: 404-406 [1990]; Cwirla et al., *Proc. Natl. Acad. Sci.* 87:6378-6382 [1990]; Felici, *J. Mol. Biol.* 222:301 [1991]).

IV. Transgenic Animals Expressing or Lacking Six1 or Cyclin A1

The present invention contemplates the generation of transgenic animals comprising an exogenous Six1 or cyclin A1 gene or mutants and variants thereof (e.g., truncations, deletions, insertions, single nucleotide polymorphisms, or heterologous Six1 or cyclin A1 genes under control of a promoter that overexpresses the gene)). In other embodiments, the present invention provides transgenic animals with a knock-out of the Six1 or cyclin A1 gene. In preferred embodiments, the transgenic animal displays an altered phenotype (e.g., increased or decreased metastasis) as compared to wild-type animals. Methods for analyzing the presence or absence of such phenotypes include but are not limited to, those disclosed herein.

The transgenic animals of the present invention find use in drug (e.g., cancer therapy) screens. In some embodiments, test compounds (e.g., a drug that is suspected of being useful to treat cancer) and control compounds (e.g., a placebo) are administered to the transgenic animals and the control animals and the effects evaluated.

The transgenic animals can be generated via a variety of methods. In some embodiments, embryonal cells at various developmental stages are used to introduce transgenes for the production of transgenic animals. Different methods are used depending on the stage of development of the embryonal cell. The zygote is the best target for micro-injection. In the mouse, the male pronucleus reaches the size of approximately 20 micrometers in diameter that allows reproducible injection of 1-2 picoliters (pl) of DNA solution. The use of zygotes as a target for gene transfer has a major advantage in that in most cases the injected DNA will be incorporated into the host genome before the first cleavage (Brinster et al., *Proc. Natl. Acad. Sci. U.S.A.* 82:4438-4442 [1985]). As a consequence, all cells of the transgenic non-human animal will carry the incorporated transgene. This will in general also be reflected in the efficient transmission of the transgene to offspring of the founder since 50% of the germ cells will harbor the transgene. U.S. Pat. No. 4,873,191 describes a method for the micro-injection of zygotes; the disclosure of this patent is incorporated herein in its entirety.

In other embodiments, retroviral infection is used to introduce transgenes into a non-human animal. In some embodiments, the retroviral vector is utilized to transfect oocytes by injecting the retroviral vector into the perivitelline space of the oocyte (U.S. Pat. No. 6,080,912, incorporated herein by reference). In other embodiments, the developing non-human embryo can be cultured in vitro to the blastocyst stage. During this time, the blastomeres can be targets for retroviral infection (Janenich, *Proc. Natl. Acad. Sci. U.S.A.* 73:1260 [1976]). Efficient infection of the blastomeres is obtained by enzymatic treatment to remove the zona pellucida (Hogan et al., in *Manipulating the Mouse Embryo*, Cold Spring Harbor Laboratory Press, Cold Spring Harbor, N.Y. [1986]). The viral vector system used to introduce the transgene is typically a replication-defective retrovirus carrying the transgene (Jahner et al., *Proc. Natl. Acad. Sci. U.S.A.* 82:6927 [1985]). Transfection is easily and efficiently obtained by culturing the blastomeres on a monolayer of virus-producing cells (Stewart, et al., *EMBO J*, 6:383 [1987]). Alternatively, infection can be performed at a later stage. Virus or virus-producing cells can be injected into the blastocoele (Jahner et al., *Nature* 298:623 [1982]). Most of the founders will be mosaic for the transgene since incorporation occurs only in a subset of cells that form the transgenic animal. Further, the founder may contain various retroviral insertions of the transgene at different positions in the genome that generally will segregate in the offspring. In addition, it is also possible to introduce transgenes into the germline, albeit with low efficiency, by intrauterine retroviral infection of the midgestation embryo (Jahner et al., supra [1982]). Additional means of using retroviruses or retroviral vectors to create transgenic animals known to the art involve the micro-injection of retroviral particles or mitomycin C-treated cells producing retrovirus into the perivitelline space of fertilized eggs or early embryos (PCT International Application WO 90/08832 [1990], and Haskell and Bowen, *Mol. Reprod. Dev.,* 40:386 [1995]).

In other embodiments, the transgene is introduced into embryonic stem cells and the transfected stem cells are utilized to form an embryo. ES cells are obtained by culturing pre-implantation embryos in vitro under appropriate conditions (Evans et al., *Nature* 292:154 [1981]; Bradley et al., *Nature* 309:255 [1984]; Gossler et al., *Proc. Acad. Sci. U.S.A.* 83:9065 [1986]; and Robertson et al., *Nature* 322:445 [1986]). Transgenes can be efficiently introduced into the ES cells by DNA transfection by a variety of methods known to the art including calcium phosphate co-precipitation, protoplast or spheroplast fusion, lipofection and DEAE-dextran-mediated transfection. Transgenes may also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (for review, See, Jaenisch, *Science* 240:1468 [1988]). Prior to the introduction of transfected ES cells into the blastocoel, the transfected ES cells may be subjected to various selection protocols to enrich for ES cells which have integrated the transgene assuming that the transgene provides a means for such selection. Alternatively, the polymerase chain reaction may be used to screen for ES cells that have integrated the transgene. This technique obviates the need for growth of the transfected ES cells under appropriate selective conditions prior to transfer into the blastocoel.

In still other embodiments, homologous recombination is utilized knock-out gene function or create deletion mutants (e.g., truncation mutants). Methods for homologous recombination are described in U.S. Pat. No. 5,614,396, incorporated herein by reference.

EXPERIMENTAL

The following examples are provided in order to demonstrate and further illustrate certain preferred embodiments and aspects of the present invention and are not to be construed as limiting the scope thereof.
Materials and Methods
Generation of Adenoviral Constructs, Adenoviral Transductions, and Microarray Analysis. Human Six1 was subcloned into pShuttle-CMV and recombinant adenovirus (Ad) was prepared as described (Liu, D., Matzuk, M. M., Sung, W. K., Guo, Q., Wang, P. & Wolgemuth, D. J. (1998) *Nat Genet* 20, 377-80). Ad-green fluorescent protein (GFP) or Ad-LacZ were used as controls. Transcriptional profiles were obtained for MCF12A (immortalized mammary epithelial) cells transduced with either Ad-Six1 or Ad-GFP at a multiplicity of infection (MOI) of 10-50 in two independent experiments. Microarray analysis was performed as described (Yam, C. H., Fung, T. K. & Poon, R. Y. (2002) *Cell Mol Life Sci* 59, 1317-26) using the Affymetrix GeneChip U133A. Intensity values were scaled such that the overall fluorescence intensity of each microarray was equivalent. Expression values below baseline were set to 20. Six1 regulated genes were defined as those whose: a) expression level at any point after infection with Ad-Six1 was greater than 3-fold above or below that in the uninfected time-zero control, in both independent experiments, b) fold change at a time point adjacent to the maximum or minimum was greater than 2, in both experiments, and c) expression level after infection with control adenovirus did not change by more than 3-fold from the uninfected time-zero control, in either experiment. For experiments using the mouse embryonic fibroblasts (MEF) from cyclin A1 knock out (Ccna1$^{-/-}$) mice, all transductions with Ad-Six1 or Ad-LacZ were carried out at a MOI of 50, and were performed at early passages (passage 5-7).

Cell Culture and Transfections. All mammary epithelial cell lines were cultured as per recommendations from the American Tissue Cell Collection (ATCC). The 21T series of cell lines (16N, 21PT, 21NT, 21MT1, and 21MT2) were cultured as previously described (15). With additional passages of the 21T series of cell lines, Six1 expression has altered such that all cancer cell lines currently express high levels of Six1 in approximately equal amounts. Six1 MCF7 stable cell lines were previously generated (15) and Six1 21PT transfectants were generated as previously described using the SLXFL plasmid (Ford, H. L., Kabingu, E. N., Bump, E. A., Mutter, G. L. & Pardee, A. B. (1998) *Proc Nat Acad Sci USA* 95, 12608-13). Control lines for MCF7 transfectants constitute one cell line transfected with Six1 but not expressing the transgene (MCF7-Control1) and two lines transfected with pcDNA3.1$^{(+)}$CAT (MCF7-Control2 and -Control3). Control lines for the 21 PT series constitute 3 stable clones transfected with pcDNA3.1$^{(+)}$LacZ. Transient transfections for siRNA experiments were performed as described (Agami, R. & Bernards, R. (2000) *Cell* 102, 55-66). The electroporator was set to pulse at 300 volts with a 2 ms burst duration instead of 140 volts and 1.5 ms, and 4 mm gap cuvettes were used rather than 1 mm gap cuvettes.

Quantitative Reverse Transcription Real-Time polymerase chain reaction (qRT-PCR), Northern blot, Reverse Transcription-PCR (RT-PCR), Immunoprecipitation, and Western blot Analyses. Total RNA from cell lines and primary breast tumors was isolated with TRIzol reagent according to the manufacturer's protocol (Invitrogen Life Tech). qRT-PCR was performed using a model 7700 instrument (Applied Biosystems). Amplicons were detected using Taqman fluorescence probes as described (Lie, Y. S. & Petropoulos, C. J. (1998) *Curr Opin Biotechnol* 9, 43-8.). Target genes were analyzed using standard curves to determine relative levels of gene expression. Individual RNA samples were normalized according to the levels of 18S rRNA. Northern blot and RT-PCR were performed as described (Ford, H. L., Kabingu, E. N., Bump, E. A., Mutter, G. L. & Pardee, A. B. (1998) *Proc Nat Acad Sci USA* 95, 12608-13; Coletta, R. D., Almeida, O. P., Grane, E., Page, R. C. & Bozzo, L. (1998) *J Periodontal Res* 33, 469-75). Primers and probes used in this study are presented in Table 2.

TABLE 2

Description of primers and probes used in the qRT-PCR, RT-PCR, and in the ChIP PCR.

| | Primer/Probe | Sequence 5' → 3' |
|---|---|---|
| For qRT-PCR | | |
| Human Six1 | Sense | CAC CTC CCC AAA GTC CAG AC (SEQ. ID. NO. 1) |
| | Antisense | CCT GGC GTG GCC CAT A (SEQ. ID. NO. 2) |
| | Probe | CGG TCC TTC TGC TGC AGG GCA T (SEQ. ID. NO. 3) |
| Mouse Six1 | Sense | AAC TGC AGC AGC TGT GGC T (SEQ. ID. NO. 4) |

TABLE 2-continued

Description of primers and probes used in the qRT-PCR, RT-PCR, and in the ChIP PCR.

| | Primer/Probe | Sequence 5' → 3' |
|---|---|---|
| | Antisense | GTC GGC CGC GAA GTT TC (SEQ. ID. NO. 5) |
| | Probe | AAA GCG CAC TAC GTG GAG GCC G (SEQ. ID. NO. 6) |
| Human cyclin A1 | Sense | GCA CCC TGC TCG TCA CTT G (SEQ. ID. NO. 7) |
| | Antisense | AGC CCC AAA TAA AAG ATC CAG (SEQ. ID. NO. 8) |
| | Probe | AGA CCG GCT TTC CCG CAA TCA TG (SEQ. ID. NO. 9) |
| Mouse cyclin A1 | Sense | TTT CCC CAA TGC TGG TTG A (SEQ. ID. NO. 10) |
| | Antisense | AAC CAA AAT CCG TTG CTT CCT (SEQ. ID. NO. 11) |
| | Probe | CCC ACC ACC CAT GCC CAG TCA (SEQ. ID. NO. 12) |
| Human cyclin A2 | Sense | TCC TCC TTG AAA AGC AAA CAG (SEQ. ID. NO. 13) |
| | Antisense | TCT TCT GAG CTT CTT TTT CTG CTT C (SEQ. ID. NO. 14) |
| | Probe | AAA CAG CCT GCG TTC ACC ATT CAT GTG (SEQ. ID. NO. 15) |
| For RT-PCR Mouse cyclin A1 | Sense | GAA GCA GCC GGA CAT CAC GGA GG (SEQ. ID. NO. 16) |
| | Antisense | CCT GAT GCA CAC TCC TTG ACG CC (SEQ. ID. NO. 17) |
| Mouse actin | Sense | TAT CCT GAC CCT GAA GTA CC (SEQ. ID. NO. 18) |
| | Antisense | GGT CAG GAT CTT CAT GAG GT (SEQ. ID. NO. 19) |
| For ChIP PCR Cyclin A1 promoter −207 to −18 | Sense | AGC TCA GCC GCA TCG CTA A (SEQ. ID. NO. 20) |
| | Antisense | ATC GCG GTT AAG AGG T (SEQ. ID. NO. 21) |
| Cyclin A1 promoter −2312 to −2107 | Sense | ATG ACC AGA GGC TTG TAA CGA C (SEQ. ID. NO. 22) |
| | Antisense | TTG ATC CAC TTT TCT GGG ATT G (SEQ. ID. NO. 23) |

Immunoprecipitation of Six1 was performed after the methods of Sauk et al. Sauk, J. J., Smith, T., Norris, K. & Ferreira, L. (1994) *J Biol Chem* 269, 3941-6). Western blot analyses using the anti-Six1 antibody were performed as described (Ford, H. L., Landesman-Bollag, E., Dacwag, C. S., Stukenberg, P. T., Pardee, A. B. & Seldin, D. C. (2000) *J Biol Chem* 275, 22245-54).

Immune-complex Kinase Assays. Histone H1 kinase assays were performed as described (Liu, D., Liao, C. & Wolgemuth, D. J. (2000) *Dev Biol* 224, 388-400). Cyclin A1, cyclin A2, and cdk2-associated kinases were immunoprecipitated using the following antibodies: cyclin A1 (23), cyclin A2 (clone BF683, Santa Cruz Biotech), cdk2 (clone D-12, Santa Cruz Biotech).

Assays of Proliferation. Cell growth and flow cytometry experiments were performed as described (Yu, Y., Khan, J., Khanna, C., Helman, L., Meltzer, P. S. & Merlino, G. (2004) *Nat Med* 10, 175-81; Coletta, R. D., Almeida, O. P., Ferreira, L. R., Reynolds, M. A. & Sauk, J. J. (1999) *Connect Tissue Res* 40, 237-49). Incorporation of bromodeoxyuridine (BrdU) was quantitated by immunofluorescence performed on cells labelled with 10 μM BrdU for 1 or 3 h.

Tumorigenicity Assays. To assess the growth of tumors in nude mouse assays, five 8-week-old nude mice per cell line were injected subcutaneously in the flank with $1 \times 10^7$ cells (MCF7-SIX1) and MCF7-Control cell lines) suspended in 100 μl medium without serum. All mice injected with MCF7 cells were supplemented with estrogen pellets (Zhang, L., Kharbanda, S., McLeskey, S. W. & Kern, F. G. (1999) *Cancer Res* 59, 5023-9), and tumor size was measured over a 6-week period. Volumes are reported as mm calculated using the formula volume=$0.5 \times \text{length} \times \text{width}^2$.

Chromatin Immunoprecipitation (CHIP) Assays. ChIP assays were performed using the Upstate Biotechnology ChIP procedure. Precipitated DNA was analyzed using PCR supplemented with 0.5 μCi $^{32}$P dCTP. Primers flanking the Six1 site of activation (−207 to −18 of cyclin A1 promoter) and the negative control site (−2312 to −2107 of cyclin A1 promoter) are described (Table 2).

Tissue Microarray, In Situ Hybridization, and Immunohistochemistry. High density breast tissues microarrays were obtained from Ambion, Inc. (Autsin, Tex.). One hundred and forty-five patients were analyzed, including 14 patients with normal mammary tissue and 131 patients with breast cancer (Breast tissue array lot # 013P09A). Both normal and tumor samples were derived from formalin-fixed, paraffin embedded tissue blocks. Expression of Six1 and cyclin A1 was assessed by in situ hybridization as described by Gurrieri et al. (Gurrieri C. Capodieci P. Bernardi R. Scaglioni P P. Nafa K. Rush L J. Verbel D A. Cordon-Cardo C. Pandolfi P P. (2004) *Journal of the National Cancer Institute* 96, 269-79, which is incorporated by reference herein in its entirety.) The expression of Six1 was graded into: 0: undetectable; 1: weak staining; 2: strong staining (overexpressed), whereas cyclin A1 was graded into 0: undetectable and 1: expressed, regardless of intensity of the staining. The proliferative potential of samples was assessed by immunohistochemical expression of Ki-67 as previously described (Coletta R. D., Cotrim P., Almeida O. P., Alves V. A., Wakamatsu A., Vargas P. A. (2002) *Oral Oncology* 38, 23-729, which is incorporated by reference herein in its entirety.) The Ki-67 index, expressed as the percentage of positive cells, was calculated by counting 100 cells from each sample.

Statistical Analyses. Analysis of variance (ANOVA) was used to test group effects, with post-hoc comparisons based on the Tukey test. The Spearman's rank correlation test ($r_s$) was assessed to verify the association between expression levels of Six1 and cyclin A1 on log-transformed values ($\text{Log}_e [x+1]$). In our comparisons, $P \leq 0.05$ was considered to indicate statistical significance.

Example 1

Six1 Activates the Cyclin A1 Promoter

Figure 6:
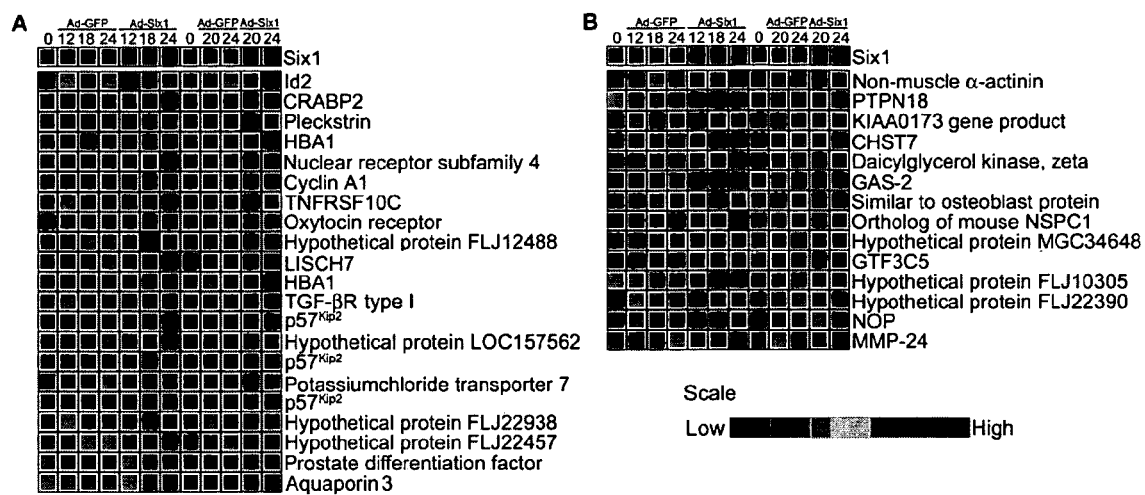
FIG. 6 shows colorgrams depicting Six1-regulated genes.

The gene expression profiles of immortalized human mammary MCF12A cells (which express low endogenous Six1 levels (FIG. 2C)) transduced with either Six1-expressing or GFP-expressing adenovirus were compared. Under criteria described above, 21 Six1 upregulated and 14 Six1 downregulated genes were identified, a subset of which are known to be important in cell cycle control (FIG. 6). In two independent experiments a Six1 dependent upregulation of the tissue-restricted cyclin A1 was observed (Howe, J. A., Howell, M., Hunt, T. & Newport, J. W. (1995) *Genes Dev* 9, 1164-76; Liu, D., Matzuk, M. M., Sung, W. K., Guo, Q., Wang, P. & Wolgemuth, D. J. (1998) *Nat Genet* 20, 377-80; Yam, C. H., Fung, T. K. & Poon, R. Y. (2002) *Cell Mol Life Sci* 59, 1317-26). Cyclin A1 has previously been shown to be expressed only in early embryogenesis (Howe, J. A., Howell, M., Hunt, T. & Newport, J. W. (1995) *Genes Dev* 9, 1164-76; Yam, C. H., Fung, T. K. & Poon, R. Y. (2002) *Cell Mol Life Sci* 59, 1317-26), in the germ-line (Liu, D., Matzuk, M. M., Sung, W. K., Guo, Q., Wang, P. & Wolgemuth, D. J. (1998) *Nat Genet* 20, 377-80), in hematopoiesis (Yang, R., Nakamaki, T., Lubbert, M., Said, J., Sakashita, A., Freyaldenhoven, B. S., Spira, S., Huynh, V., Muller, C. & Koeffler, H. P. (1999) *Blood* 93, 2067-74), and in the brain (Yang, R., Morosetti, R. & Koeffler, H. P. (1997) *Cancer Res* 57, 913-20). Neither c-Myc nor Gdnf, previously identified Six1 targets in C2C12 cells (Li, X., Oghi, K. A., Zhang, J., Krones, A., Bush, K. T., Glass, C. K., Nigam, S. K., Aggarwal, A. K., Maas, R., Rose, D. W. & Rosenfeld, M. G. (2003) *Nature* 426, 247-54) were upregulated when MCF12A mammary epithelial cells were transduced with Six1. In addition to cyclin A1, $p57^{kip2}$, a cyclin dependent kinase inhibitor, was upregulated by Six1.

To determine whether Six1 activates the cyclin A1 promoter, MCF7 mammary carcinoma cells were transfected with a full-length human cyclin A1 promoter-luciferase reporter construct (Muller, C., Yang, R., Beck-von-Peccoz, L., Idos, G., Verbeek, W. & Koeffler, H. P. (1999) *J Biol Chem* 274, 11220-8) in the presence of increasing concentrations of a Six1 expression plasmid. Six1 transactivated the cyclin A1 promoter in a dose-dependent manner, with activation reaching 12-fold at the highest concentration (FIG. 1A). To delineate the region within the cyclin A1 promoter through which Six1 confers its activity, cyclin A1 promoter deletion constructs (Muller, C., Yang, R., Beck-von-Peccoz, L., Idos, G., Verbeek, W. & Koeffler, H. P. (1999) *J Biol Chem* 274, 11220-8) and Six1 expression constructs were co-transfected into MCF7 cells and luciferase assays were performed. The region between −37 and −112 of the cyclin A1 promoter was identified as necessary for activation by Six1 (FIG. 1B). This region does not contain a described consensus sequence for Six1 DNA binding (ATCCTGA) (Li, X., Oghi, K. A., Zhang, J., Krones, A., Bush, K. T., Glass, C. K., Nigam, S. K., Aggarwal, A. K., Maas, R., Rose, D. W. & Rosenfeld, M. G. (2003) *Nature* 426, 247-54; Spitz, F., Demignon, J., Porteu, A., Kahn, A., Concordet, J. P., Daegelen, D. & Maire, P. (1998) *Proc Natl Acad Sci USA* 95, 14220-5). Binding of Six1 within the −37 to −112 region of the cyclin A1 promoter was confirmed via ChIP assays from the 21PT mammary carcinoma cell line, a line that expresses high endogenous levels of Six1 (FIG. 1C). These results demonstrate that Six1 activates cyclin A1 through an interaction with the cyclin A1 promoter.

Example 2

Figure 2:
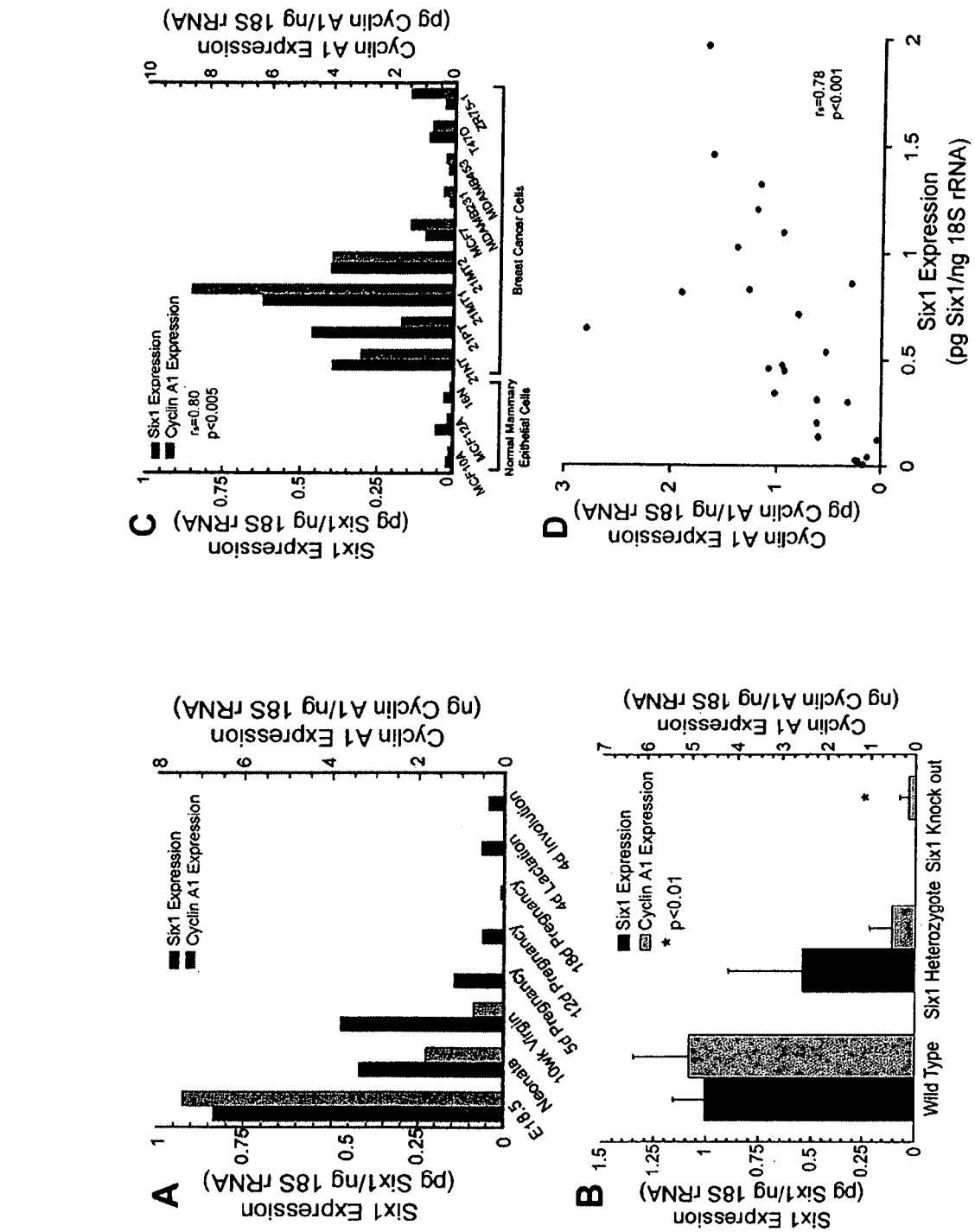
FIG. 2A shows that Six1 and cyclin A1 are expressed in the embryonic mammary gland but not fully differentiated adult pregnant and lactating mammary gland.
FIG. 2B shows reduction of cyclin A1 in Six1 knockout mammary glands.
FIG. 2C shows that Six1 and cyclin A1 mRNA levels are expressed in multiple breast cancer cell lines, but not in immortalized normal breast cell lines.
FIG. 2D shows that cyclin A1 levels correlate with Six1 in breast cancer samples by qRT-PCR.

Six1 and Cyclin A1 are Co-Ordinately Regulated During Mammary Gland Development and Tumorigenesis Cyclin A1 is implicated in cell cycle control in early embryogenesis and in germ cells (Howe, J. A., Howell, M., Hunt, T. & Newport, J. W. (1995) *Genes Dev* 9, 1164-76; Liu, D., Matzuk, M. M., Sung, W. K., Guo, Q., Wang, P. & Wolgemuth, D. J. (1998) *Nat Genet* 20, 377-80; Yam, C. H., Fung, T. K. & Poon, R. Y. (2002) *Cell Mol Life Sci* 59, 1317-26). To determine whether both Six1 and cyclin A1 are expressed in the developing mammary gland, we examined their expression throughout mammary gland development by qRT-PCR. Both Six1 and cyclin A1 are highly expressed in the embryonic mammary gland at day 18.5, with levels decreasing after birth (FIG. 2A). Cyclin A1 levels are dramatically reduced by the time of maturity (10 weeks), while Six1 levels decline more slowly. By the time the mammary gland is fully differentiated (pregnancy), very little Six1 expression is observed (FIG. 2A). Embryonic day 18.5 mammary glands from Six1 knockout mice (Ozaki, H., Nakamura, K., Funahashi, J., Ikeda, K., Yamada, G., Tokano, H., Okamura, H. O., Kitamura, K., Muto, S., Kotaki, H., Sudo, K., Horai, R., Iwakura, Y. & Kawakami, K. (2004) *Development* 131, 551-62) have a greater than 90% reduction in cyclin A1 mRNA as compared to wild type embryonic day 18.5 mammary glands (FIG. 2B), demonstrating that Six1 is upstream of cyclin A1 in vivo. The restriction of cyclin A1 to the embryonic mammary gland is consistent with published data demonstrating that this A-type cyclin is relatively specific to embryogenesis and the germ line, as opposed to most adult somatic cells (Howe, J. A., Howell, M., Hunt, T. & Newport, J. W. (1995) *Genes Dev* 9, 1164-76; Liu, D., Matzuk, M. M., Sung, W. K., Guo, Q., Wang, P. & Wolgemuth, D. J. (1998) *Nat Genet* 20, 377-80; Yam, C. H., Fung, T. K. & Poon, R. Y. (2002) *Cell Mol Life Sci* 59, 1317-26).

To determine the expression levels of Six1 and cyclin A1 in a pure mammary epithelial population, we performed qRT-PCR for both Six1 and cyclin A1 in immortalized mammary epithelial cell lines. Expression of both Six1 and cyclin A1 in human mammary epithelial cell lines MCF10A, MCF12A, and 16N is very low (FIG. 2C), consistent with in vivo data demonstrating that these genes are not highly expressed in the adult mammary gland (FIG. 2A). In contrast, Six1 levels are dramatically increased in human mammary carcinoma cell lines, and this increase correlates with an increase in cyclin A1 expression ($r_s$=0.80, p<0.005; FIG. 2B). Furthermore, analysis of 25 primary breast cancer samples for Six1 and cyclin A1 expression demonstrates a statistically significant correlation between the two ($r_s$=0.78, p<0.001; FIG. 2C).

Example 3

Six1 Induces Cellular Proliferation and Increases Tumor Volume in Nude Mice

Figure 3:
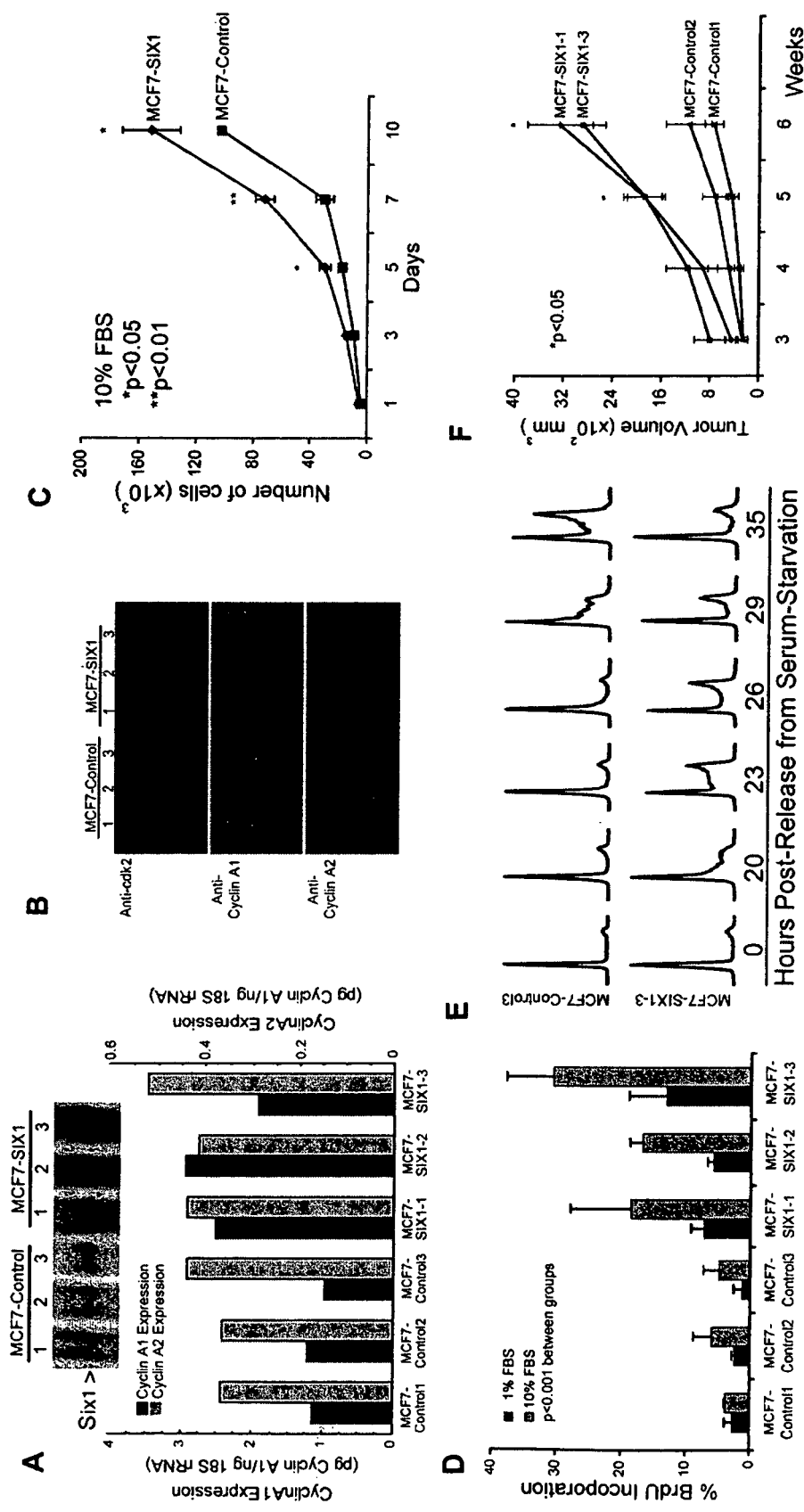
FIG. 3A shows increased levels of cyclin A1 mRNA in MCF7-SIX1 transfectants compared to controls. The top panel shows immunoprecipitation of Six1 in MCF7-SIX1 and MCF7-Control transfectants, whereas the bottom panel demonstrates via qRT-PCR that cyclin A1 levels are increased in the Six1-transfectants, while cyclin A2 levels remain unchanged
FIG. 3B shows an increase in cyclin A1- and cdk2-associated kinase activities in Six1 overexpressing MCF7 cells, whereas cyclin A2-associated kinase activity remains unchanged.
FIG. 3C shows assays measuring cell growth.
FIG. 3D shows by BrdU incorporation that Six1 overexpressing cell lines have a statistically significant increase in proliferation as compared to control cells.
FIG. 3E shows representative flow cytometry of one Six1 overexpressing (MCF7-SIX1-3) and one control (MCF7-Control 3) transfectant demonstrating that overexpression of Six1 accelerates cell cycle progression in MCF7 cells.
FIG. 3F shows that expression of Six1 significantly increases tumor burden in nude mice.
Figure 7:
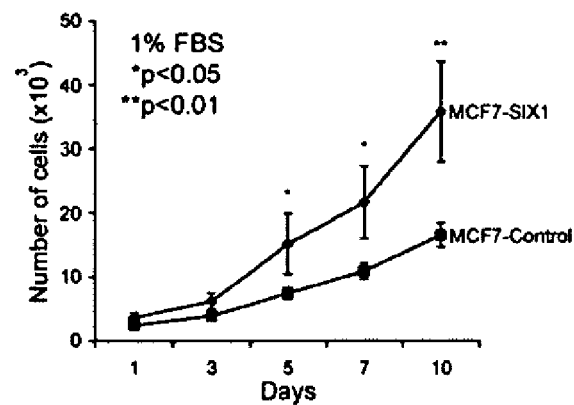
FIG. 7 shows that Six1 overexpression increases the growth rate of MCF7 cells at low serum conditions.
Figure 8:
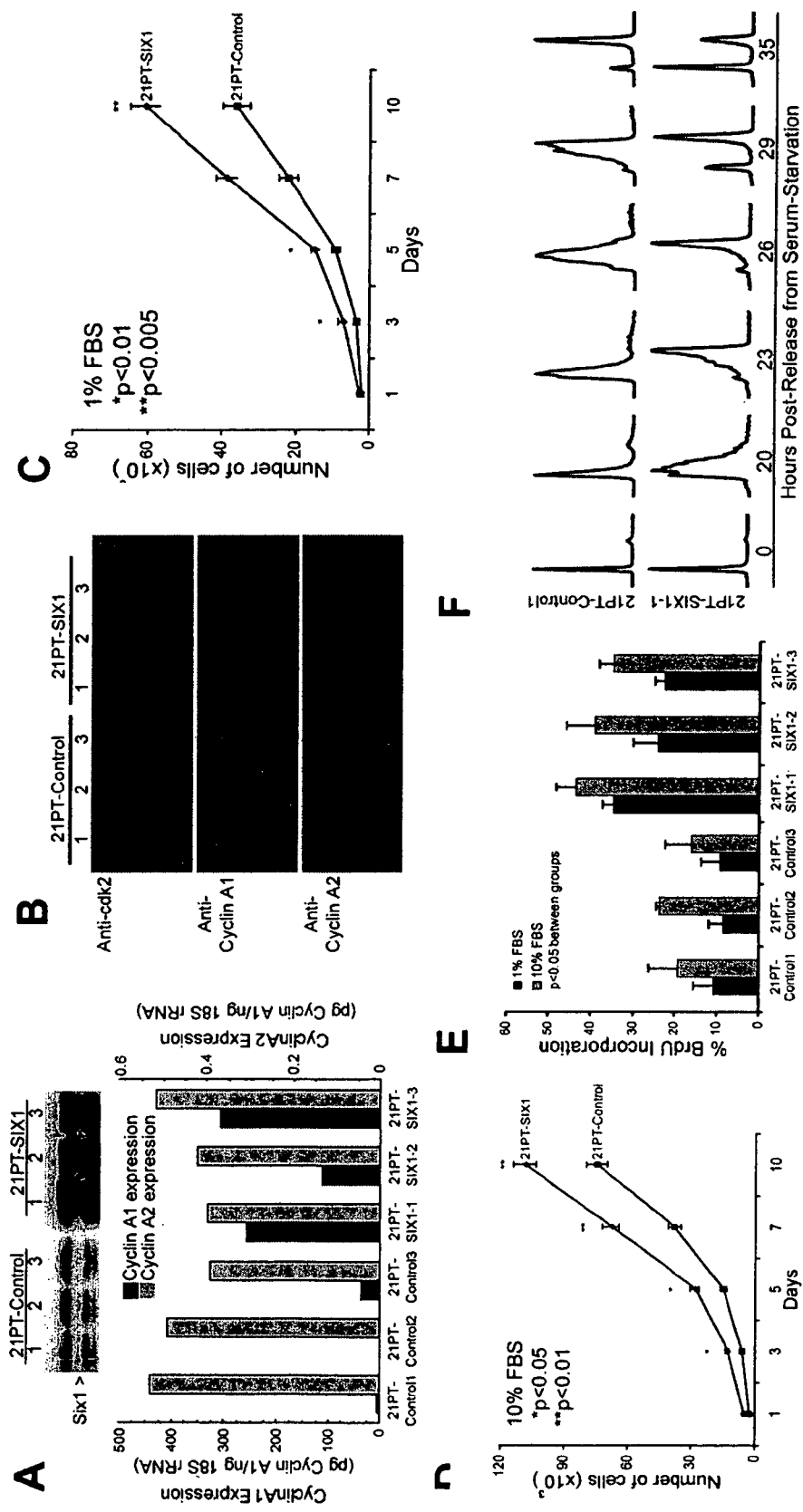
FIG. 8A shows by Western blot and qRT-PCR analyses that overexpression of Six1 induces cyclin A1 expression. The top panel represents a Western blot using the Six1 antibody to examine Six1 protein levels in control or Six1 stable 21PT transfectants. The bottom panel represents cyclin A1 and cyclin A2 mRNA levels in the same cell lines as measured by qRT-PCR.
FIG. 8B shows immune-complex kinase assays demonstrating an increase in cyclin A1- and cdk2-associated kinase activities in Six1 overexpressing 21PT cells, whereas cyclin A2-associated kinase activity remains unchanged.
FIG. 8C shows that 21PT cells overexpressing Six1 have an increased growth rate as compared to control transfectants in 1% serum.
FIG. 8D shows that 21PT cells overexpressing Six1 have an increased growth rate as compared to control transfectants in 10% serum.
FIG. 8E shows that proliferation is increased in Six1 overexpressing 21PT cells as measured by BrdU incorporation index corresponding to the mean percentage of positive cells in S-phase of the cell cycle.
FIG. 8F shows by flow cytometry analysis of 21PT cells that overexpressing Six1 causes an accelerated progression through the cell cycle.

Cyclin A1 binds to and activates both cdk2 and cdk1 (Sweeney, C., Murphy, M., Kubelka, M., Ravnik, S. E., Hawkins, C. F., Wolgemuth, D. J. & Carrington, M. (1996) *Development* 122, 53-64), and has been implicated both in entrance into and progression through S-phase as well as in the G2/M transition (Liu, D., Liao, C. & Wolgemuth, D. J. (2000) *Dev Biol* 224, 388-400; Yang, R., Muller, C., Huynh, V., Fung, Y. K., Yee, A. S. & Koeffler, H. P. (1999) *Mol Cell Biol* 19, 2400-7; Romanowski, P., Marr, J., Madine, M. A., Rowles, A., Blow, J. J., Gautier, J. & Laskey, R. A. (2000) *J Biol Chem* 275, 4239-43). Six1 overexpression results in an attenuation of the G2 checkpoint (Ford, H. L., Kabingu, E. N., Bump, E. A., Mutter, G. L. & Pardee, A. B. (1998) *Proc Natl Acad Sci USA* 95, 12608-13), a phenotype consistent with overexpression of an A-type cyclin (Guo, N., Faller, D. V. & Vaziri, C. (2000) *J Biol Chem* 275, 1715-22; Goldstone, S., Pavey, S., Forrest, A., Sinnamon, J. & Gabrielli, B. (2001) *Oncogene* 20, 921-32). Examination of both Six1 mRNA and protein levels throughout the cell cycle demonstrate its presence as early as the G1/S boundary, and its continued increase as cells progress through S-phase and into mitosis. Furthermore, Six1 is a target of E2F1, a transcription factor known to be critical for the G1/S transition (Young, A. P., Nagarajan, R. & Longmore, G. D. (2003) *Oncogene* 22, 7209-17). Stable MCF7 transfectants overexpressing Six1 or control transfectants were examined for their proliferative potential as well as for cyclin A1 expression. FIG. 3A demonstrates overexpression of the Six1 protein in stable MCF7-SIX1 cell lines. These lines also overexpress cyclin A1 mRNA approximately 2-3 fold whereas cyclin A2 levels are unchanged (FIG. 3A). Consistent with the increase in cyclin A1 mRNA, cyclin A1-associated and cdk2-associated kinase activities are increased in the Six1 overexpressing cell lines, whereas cyclin A2-associated kinase activity remains unchanged (FIG. 3B). Six1 overexpressing cells have a statistically significant increase in proliferation (FIGS. 3C and 3D, and FIG. 7), and an acceleration in cell cycle progression that occurs as early as the G1/S transition is observed these cells (FIG. 3E). This acceleration demonstrates that effects of Six1 on the cell cycle are not confined to the G2/M transition. Similar results were obtained in a different mammary carcinoma cell line stably overexpressing Six1 (FIG. 8A-F). When MCF7-SIX1 cell lines were injected into nude mice, tumors formed were significantly larger than those formed by the MCF7-Control cells (FIG. 3F). These data demonstrate that Six1 overexpression in mammary carcinoma cells results in hyperproliferation and a greater tumor burden, consistent with an increase in proliferation as the result of a direct activation of cyclin A1.

Figure 4:
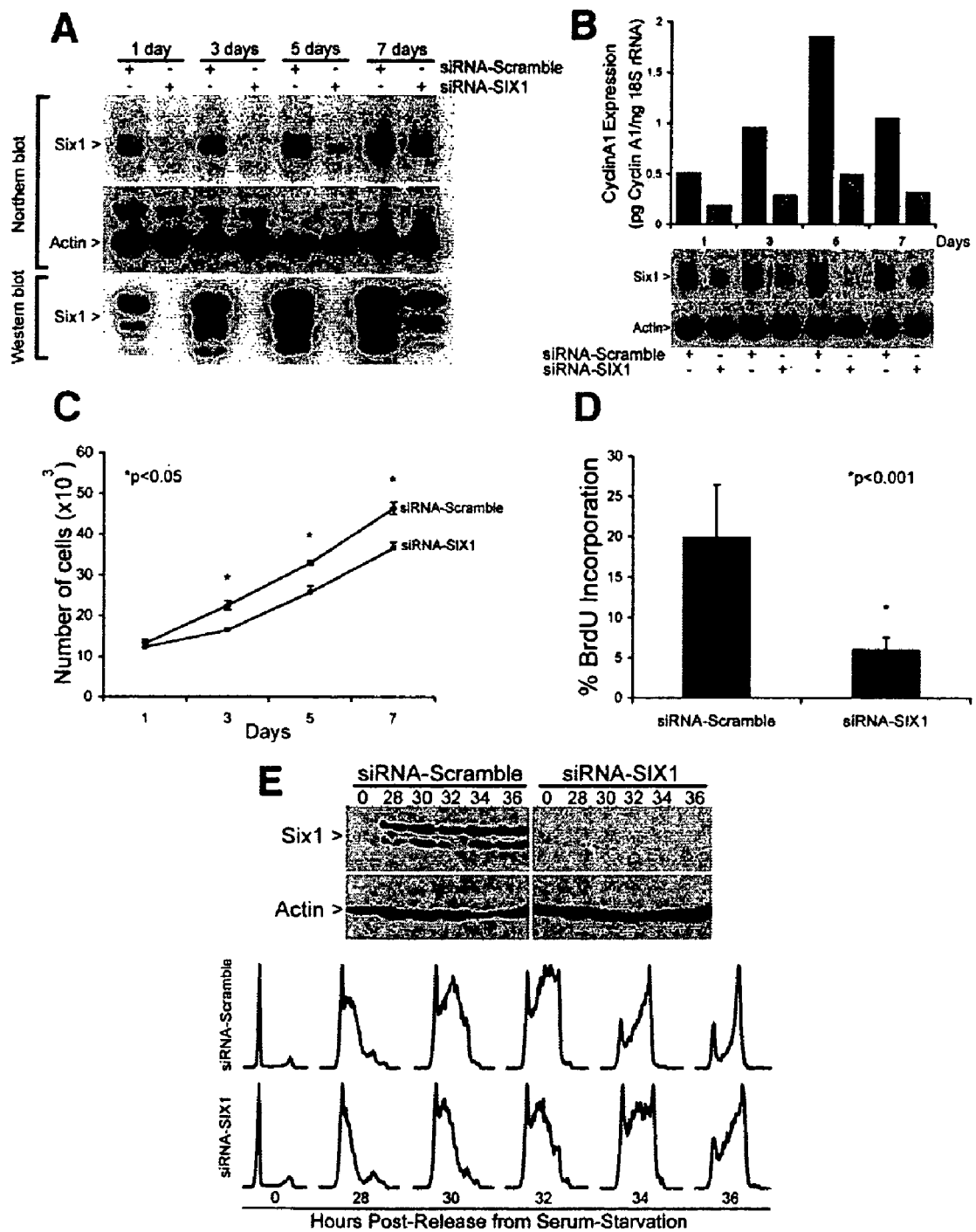
FIG. 4A shows that siRNA against Six1 decreases Six1 levels over a 7-day time course and that Northern blot (Six1 and actin) and Western blot (Six1) analysis demonstrate that Six1 levels are decreased after introduction of the siRNA-SIX1 construct.
FIG. 4B shows by qRT-PCR and Northern blot analyses a decrease in cyclin A1 expression (top panel) when Six1 is inhibited (bottom panels).
FIG. 4C shows a statistically significant decrease in proliferation by cell growth when Six1 is downregulated via siRNA.
FIG. 4D shows a statistically significant decrease in proliferation by BrdU incorporation when Six1 is downregulated via siRNA.
FIG. 4E shows a slower progression through the cell cycle when Six1 is downregulated, as demonstrated by flow cytometry on propidium iodide-stained cells The inset represents Six1 protein levels over the time course.

To determine whether the endogenous function of Six1 is to promote proliferation, Six1 was knocked down in mammary carcinoma cells expressing high levels of the gene (21PT cells). Using the pSUPER system and a high efficiency electroporation protocol (Brummelkamp, T. R., Bernards, R. & Agami, R. (2002) *Science* 296, 550-3.), vectors expressing either a Six1 specific double stranded RNA (designed to target the Six1 mRNA at base pairs 409-428), or a scrambled version of the same RNA molecule, were transfected into 21PT cells. When the Six1 specific vector was used, a rapid downregulation of Six1 mRNA and protein was observed and maintained over a 7-day time course (FIG. 4A). The decrease in Six1 levels resulted in a concomitant decrease in cyclin A1 mRNA, demonstrating that endogenous Six1 regulates cyclin A1 mRNA levels (FIG. 4B). Cell growth assays and BrdU incorporation assays showed a statistically significant decrease in proliferation when Six1 was downregulated with siRNA (FIGS. 4C and 4D). Whereas Six1 overexpression accelerated cell cycle progression, a decrease in Six1 levels slowed the progression of cells through the cell cycle (FIG. 4E).

Example 4

Six1 is Dependent on Cyclin A1 to Stimulate Cellular Proliferation

Figure 5:
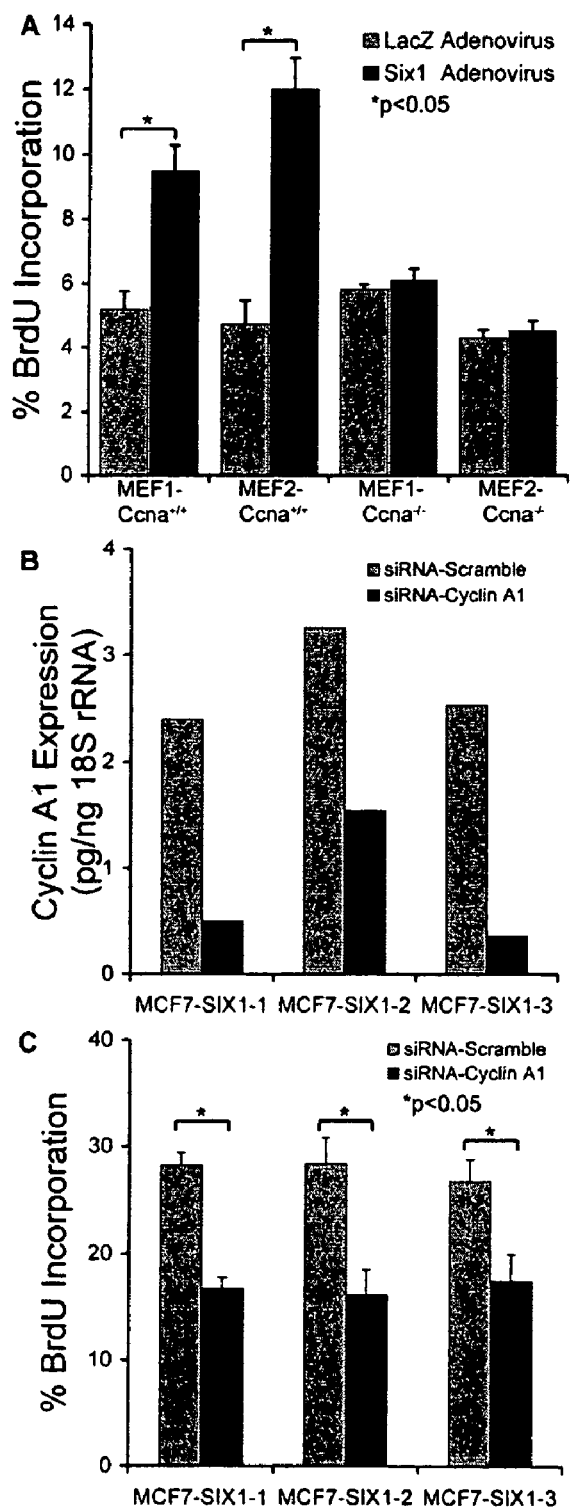
FIG. 5A shows BrdU incorporation assays demonstrating the dependency of Six1 on cyclin A1 for inducing cellular proliferation, as wild type cells (MEF-Ccna1$^{+/+}$) can be stimulated to increase proliferation when Six1 is introduced via adenoviral transduction, whereas cyclin A-deficient cells (MEF-Ccna1$^{-/-}$) cannot be induced to proliferate via the introduction of Six1.
FIG. 5B shows that cyclin A1 mRNA is reduced in Six1 overexpressing MCF7 cells after introduction of a cyclin A1 siRNA to levels at or slightly below levels observed in CAT transfected controls (see FIG. 3A).
FIG. 5C shows that proliferation is decreased in MCF-SIX1 cells when cyclin A1 levels are reduced via siRNA with proliferation measured via BrdU incorporation.
Figure 9:
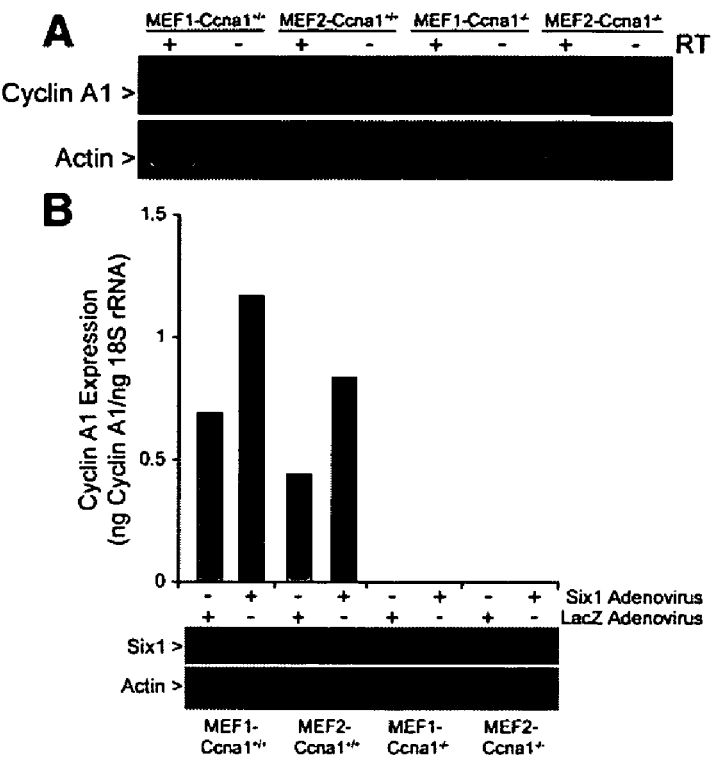
FIG. 9A shows by reverse transcription-PCR that wild type cells express cyclin A1 (MEF-Ccna1$^{+/+}$), whereas cyclin A1-deficient cells (MEF-Ccna1$^{-/-}$) do not.
FIG. 9B shows by qRT-PCR that cyclin A1 is induced in MEF-Ccna1$^{+/+}$ after the introduction of a Six1 containing adenovirus, whereas it is not induced with the Six1 adenovirus in the MEF-Ccna$^{-/-}$. The Northern blot analysis depicts amount of Six1 mRNA introduced into MEF following adenoviral transduction.

To determine whether activation of cyclin A1 by Six1 is required for the proliferative effect of Six1, MEFs were established from wild type (Ccna1$^{+/+}$) and cyclin A1-deficient (Ccna1$^{-/-}$) mice. The presence of cyclin A1 in two independent MEF-Ccna1$^{+/+}$ clones, and its absence in two independent MEF-Ccna1$^{-/-}$ clones, was confirmed by RT-PCR (FIG. 9A). When Six1 was introduced into MEF-Ccna1$^{+/+}$ via adenoviral transduction, cyclin A1 levels were increased, whereas no increase was observed in the MEF-Ccna1$^{-/-}$ clones (FIG. 9B). Transduction of Six1 into MEF-Ccna1$^{+/+}$ led to an increase in proliferation, as measured by BrdU incorporation, as compared to control transduced MEFs (FIG. 5A). In contrast, introduction of Six1 into cyclin A1-deficient MEF did not result in an increase in proliferation (FIG. 5A), demonstrating that Six1 mediates its effects on proliferation via the induction of cyclin A1.

Figure 10:
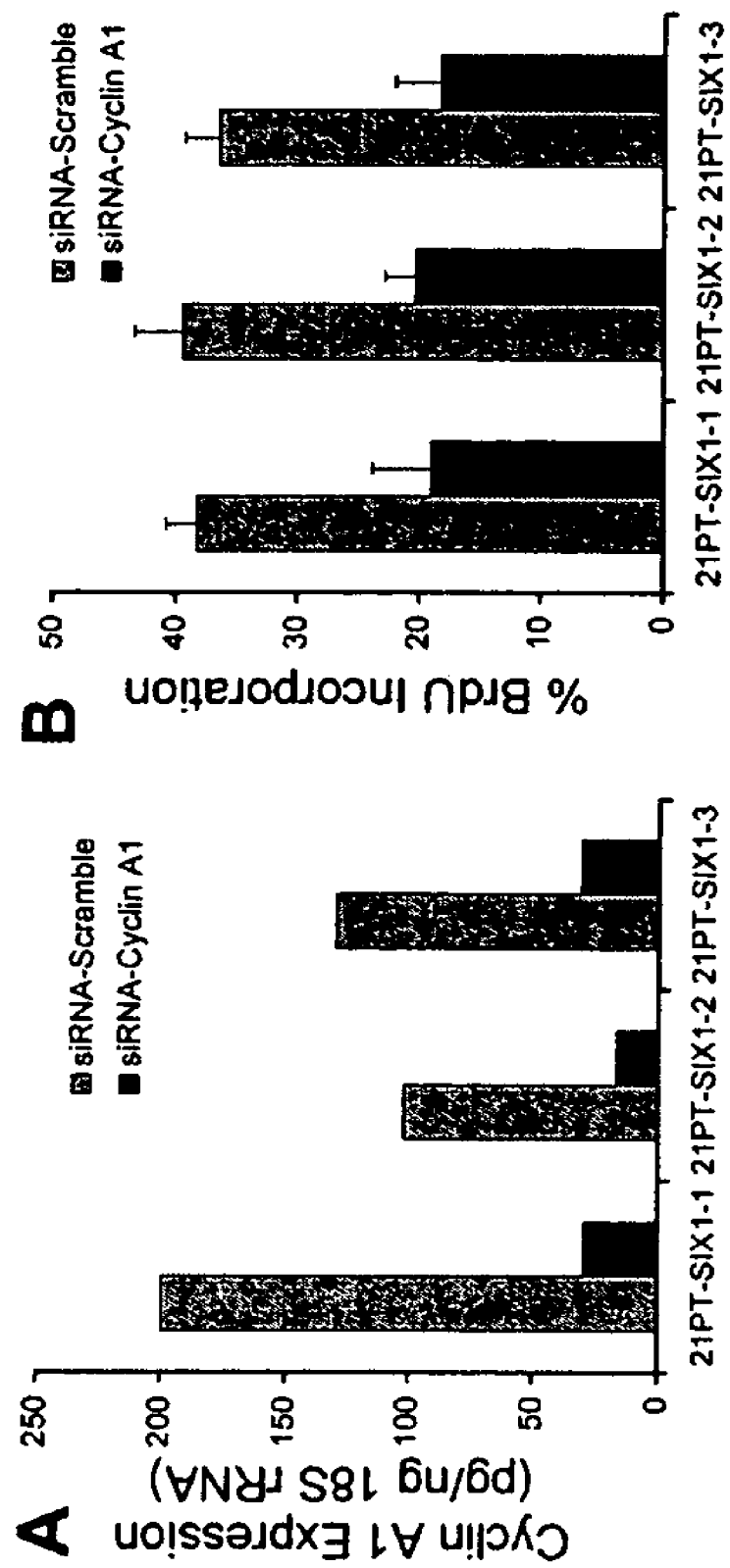
FIG. 10 B shows that cellular proliferation measured via BrdU incorporation is decreased in Six1 overexpressing 21PT cells when cyclin A1 levels are reduced via siRNA.

To demonstrate that proliferation of Six1-overexpressing mammary carcinoma cells is dependent on cyclin A1, cyclin A1 was knocked down via siRNA in MCF7-SIX1 cells to levels similar to that observed in MCF-CAT cells. FIG. 5B demonstrates the levels of cyclin A1 mRNA in MCF7-SIX cells treated with a cyclin A1 scrambled siRNA vector as a control, or a siRNA vector targeting cyclin A1 (designed to target the cyclin A1 mRNA at base pairs 939-958). When cyclin A1 levels were diminished in Six1-overexpressing mammary carcinoma cells, proliferation, as measured by BrdU incorporation, significantly decreased (FIG. 5C). This result was recapitulated in the Six1-overexpressing 21PT mammary carcinoma cells (FIG. 10 A-B). Together, these results demonstrate the dependence of Six1 on cyclin A1 for mediating proliferation in mammary carcinoma cells.

Example 5

Six1 Stimulates Proliferation of Breast Tumor Cells Via Induction of Cyclin A1

To determine whether there is a correlation between Six1, cyclin A1 and the proliferative potential of breast tumor cells, rank correlation was performed on these parameters following in situ hybridization for Six1 and cyclin A1, and antibody staining for Ki-67 (a marker of proliferation) in breast cancer (n=131) and normal breast (n=14) samples. The results demonstrate that there is a strong correlation between Six1 and cyclin A1 expression in normal and cancerous breast samples ($r_s$=0.62, p<0.01), as well as between Six1 and the proliferative marker Ki-67 ($r_s$=0.45, p<0.05), and between cyclin A1 and Ki-67 ($r_s$=0.59, p<0.01). This data indicates that Six1 may stimulate proliferation of breast tumor cells via induction of cyclin A1.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A method for reducing cyclin A1 mRNA level in a subject, comprising
   a) providing:
      i) a subject with one or more signs or symptoms of carcinoma; and
      ii) a preparation comprising Six1 siRNA,
   b) administering said preparation comprising said Six1 siRNA to said subject to produce a treated subject, wherein said administering is under conditions such that the amount of cyclin A1 mRNA is reduced in said treated subject, and
   c) measuring a reduced level of cyclin A1 mRNA in said treated subject.

2. The method of claim 1, wherein said subject has breast cancer.

* * * * *

SEQUENCE LISTING

<160> NUMBER OF SEQ ID NOS: 23

<210> SEQ ID NO 1

```
<211> LENGTH: 20
<212> TYPE: DNA
<213> ORGANISM: Homo sapiens

<400> SEQUENCE: 1 cacctccccca aagtccagac                                              20

<210> SEQ ID NO 2
<211> LENGTH: 16
<212> TYPE: DNA
<213> ORGANISM: Homo sapiens

<400> SEQUENCE: 2
cctggcgtgg cccata                                                   16

<210> SEQ ID NO 3
<211> LENGTH: 22
<212> TYPE: DNA
<213> ORGANISM: Homo sapiens

<400> SEQUENCE: 3
cggtccttct gctgcagggc at                                            22

<210> SEQ ID NO 4
<211> LENGTH: 19
<212> TYPE: DNA
<213> ORGANISM: Mus musculus

<400> SEQUENCE: 4
aactgcagca gctgtggct                                                19

<210> SEQ ID NO 5
<211> LENGTH: 17
<212> TYPE: DNA
<213> ORGANISM: Mus musculus

<400> SEQUENCE: 5
gtcggccgcg aagtttc                                                  17

<210> SEQ ID NO 6
<211> LENGTH: 22
<212> TYPE: DNA
<213> ORGANISM: Mus musculus

<400> SEQUENCE: 6
aaagcgcact acgtggaggc cg                                            22

<210> SEQ ID NO 7
<211> LENGTH: 19
<212> TYPE: DNA
<213> ORGANISM: Homo sapiens

<400> SEQUENCE: 7
gcaccctgct cgtcacttg                                                19

<210> SEQ ID NO 8
<211> LENGTH: 21
<212> TYPE: DNA
<213> ORGANISM: Homo sapiens

<400> SEQUENCE: 8
agcccccaat aaaagatcca g                                             21

<210> SEQ ID NO 9
```

```
<211> LENGTH: 23
<212> TYPE: DNA
<213> ORGANISM: Homo sapiens

<400> SEQUENCE: 9
agaccggctt tcccgcaatc atg                                              23

<210> SEQ ID NO 10
<211> LENGTH: 19
<212> TYPE: DNA
<213> ORGANISM: Mus musculus

<400> SEQUENCE: 10
tttccccaat gctggttga                                                   19

<210> SEQ ID NO 11
<211> LENGTH: 21
<212> TYPE: DNA
<213> ORGANISM: Mus musculus

<400> SEQUENCE: 11
aaccaaaatc cgttgcttcc t                                                21

<210> SEQ ID NO 12
<211> LENGTH: 21
<212> TYPE: DNA
<213> ORGANISM: Mus musculus

<400> SEQUENCE: 12
cccaccaccc atgcccagtc a                                                21

<210> SEQ ID NO 13
<211> LENGTH: 21
<212> TYPE: DNA
<213> ORGANISM: Homo sapiens

<400> SEQUENCE: 13
tcctccttgg aaagcaaaca g                                                21

<210> SEQ ID NO 14
<211> LENGTH: 25
<212> TYPE: DNA
<213> ORGANISM: Homo sapiens

<400> SEQUENCE: 14
tcttctgagc ttcttttct gcttc                                             25

<210> SEQ ID NO 15
<211> LENGTH: 27
<212> TYPE: DNA
<213> ORGANISM: Homo sapiens

<400> SEQUENCE: 15
aaacagcctg cgttcaccat tcatgtg                                          27

<210> SEQ ID NO 16
<211> LENGTH: 23
<212> TYPE: DNA
<213> ORGANISM: Mus musculus

<400> SEQUENCE: 16
gaagcagccg gacatcacgg agg                                              23

<210> SEQ ID NO 17
```

```
<211> LENGTH: 23
<212> TYPE: DNA
<213> ORGANISM: Mus musculus

<400> SEQUENCE: 17
cctgatgcac actccttgac gcc                                               23

<210> SEQ ID NO 18
<211> LENGTH: 20
<212> TYPE: DNA
<213> ORGANISM: Mus musculus

<400> SEQUENCE: 18
tatcctgacc ctgaagtacc                                                   20

<210> SEQ ID NO 19
<211> LENGTH: 20
<212> TYPE: DNA
<213> ORGANISM: Mus musculus

<400> SEQUENCE: 19
ggtcaggatc ttcatgaggt                                                   20

<210> SEQ ID NO 20
<211> LENGTH: 19
<212> TYPE: DNA
<213> ORGANISM: Homo sapiens

<400> SEQUENCE: 20
agctcagccg catcgctaa                                                    19

<210> SEQ ID NO 21
<211> LENGTH: 16
<212> TYPE: DNA
<213> ORGANISM: Homo sapiens

<400> SEQUENCE: 21
atcgcggtta agaggt                                                       16

<210> SEQ ID NO 22
<211> LENGTH: 22
<212> TYPE: DNA
<213> ORGANISM: Homo sapiens

<400> SEQUENCE: 22
atgaccagag gcttgtaacg ac                                                22

<210> SEQ ID NO 23
<211> LENGTH: 22
<212> TYPE: DNA
<213> ORGANISM: Homo sapiens

<400> SEQUENCE: 23
ttgatccact tttctgggat tg                                                22
```